(12) United States Patent
Utku

(10) Patent No.: US 7,794,715 B2
(45) Date of Patent: Sep. 14, 2010

(54) ANTI-TIRC7 ANTIBODIES IN THERAPY OF INFLAMMATORY DISEASES

(75) Inventor: Nalan Utku, Berlin (DE)

(73) Assignee: CellAct Pharma GmbH, Dortmund (DE)

( * ) Notice: Subject to any disclaimer, the term of this patent is extended or adjusted under 35 U.S.C. 154(b) by 1338 days.

(21) Appl. No.: 10/513,611

(22) PCT Filed: Dec. 23, 2002

(86) PCT No.: PCT/EP02/14733

§ 371 (c)(1),
(2), (4) Date: Aug. 8, 2005

(87) PCT Pub. No.: WO03/054018

PCT Pub. Date: Jul. 3, 2003

(65) Prior Publication Data

US 2006/0251646 A1 Nov. 9, 2006

(30) Foreign Application Priority Data

| Dec. 21, 2001 | (EP) | ................................. | 01130730 |
| Jun. 17, 2002 | (EP) | ................................. | 02013261 |
| Aug. 22, 2002 | (EP) | ................................. | 02018809 |

(51) Int. Cl.
*A61K 39/395* (2006.01)

(52) U.S. Cl. .............. 424/133.1; 424/143.1; 424/154.1; 530/387.3; 530/388.22; 530/388.75

(58) Field of Classification Search .................. None
See application file for complete search history.

(56) References Cited

U.S. PATENT DOCUMENTS

| 5,994,510 A * | 11/1999 | Adair et al. ............... 530/387.3 |
| 6,090,382 A * | 7/2000 | Salfeld et al. ............ 424/133.1 |
| 2006/0165684 A1 * | 7/2006 | Utku .......................... 424/143.1 |

FOREIGN PATENT DOCUMENTS

| DE | 19738710 A1 | 3/1999 |
| EP | 387095 A1 * | 9/1990 |
| WO | WO 99/11782 | 3/1999 |
| WO | WO 9911782 A1 * | 3/1999 |
| WO | WO 02/36149 A2 | 5/2002 |
| WO | WO 03/025000 A2 | 3/2003 |

OTHER PUBLICATIONS

Portolano et al., J Immunol. Feb. 1, 1993;150(3):880-7.*
Van den Beucken et al., J Mol Biol. Jul. 13, 2001;310(3):591-601.*
PR Newswire, "Abbott Laboratories Receives FDA Approval Earlier Than Anticipated for HUMIRA(™) (adalimumab) for the Treatment of Rheumatoid Arthritis (RA)," Dec. 31, 2002, pp. 1-4.*
Grubb R: Human immunoglobulin allotypes and Mendelian polymorphism of the human immunoglobulin genes; in Oss CJ, Regenmortel MHV (eds): Immunochemistry, New York, Dekker, 1994, pp. 47-68.*
Ziwei Huang, Pharmacol Ther. Jun. 2000;86(3):201-15.*
Satoh et al., J Biol Chem. May 1997 2;272(18):12175-80.*
Li et al., J Biol Chem. Jun. 26, 1998;273(26):16442-5.*
Taylor et al., Curr Opin Rheumatol. May 2001;13(3):164-9.*
Utku et al., (1998) "Prevention of Acute Allograft Rejection by Antibody Targeting of TIRC7 a Novel T Cell Membrane Protein" Immunity, vol. 9, pp. 509-518.
International Search Report issued Dec. 29, 2003 in connection with PCT International Application No. PCT/EP02/14733.

* cited by examiner

*Primary Examiner*—Zachary Skelding
(74) *Attorney, Agent, or Firm*—John P. White; Cooper & Dunham LLP

(57) ABSTRACT

A method for the treatment of inflammatory disorders is disclosed, particularly the treatment of arthritis. The method comprises particular therapeutic and preventive treatment regimens for the administration of a T-cell immune response cDNA 7 (TIRC7) antagonist, preferably an anti-TIRC7 antibody. Particularly useful monoclonal, in particular chimeric anti-TIRC7 antibodies are described. Furthermore, a combination therapy for the treatment of an inflammatory disease, particularly rheumatoid arthritis, is provided involving the use of TIRC7 antagonist, such as anti-TIRC7 antibody in conjunction with an anti-inflammatory drug such as TNF-α antagonist.

4 Claims, 10 Drawing Sheets

Figure 3:
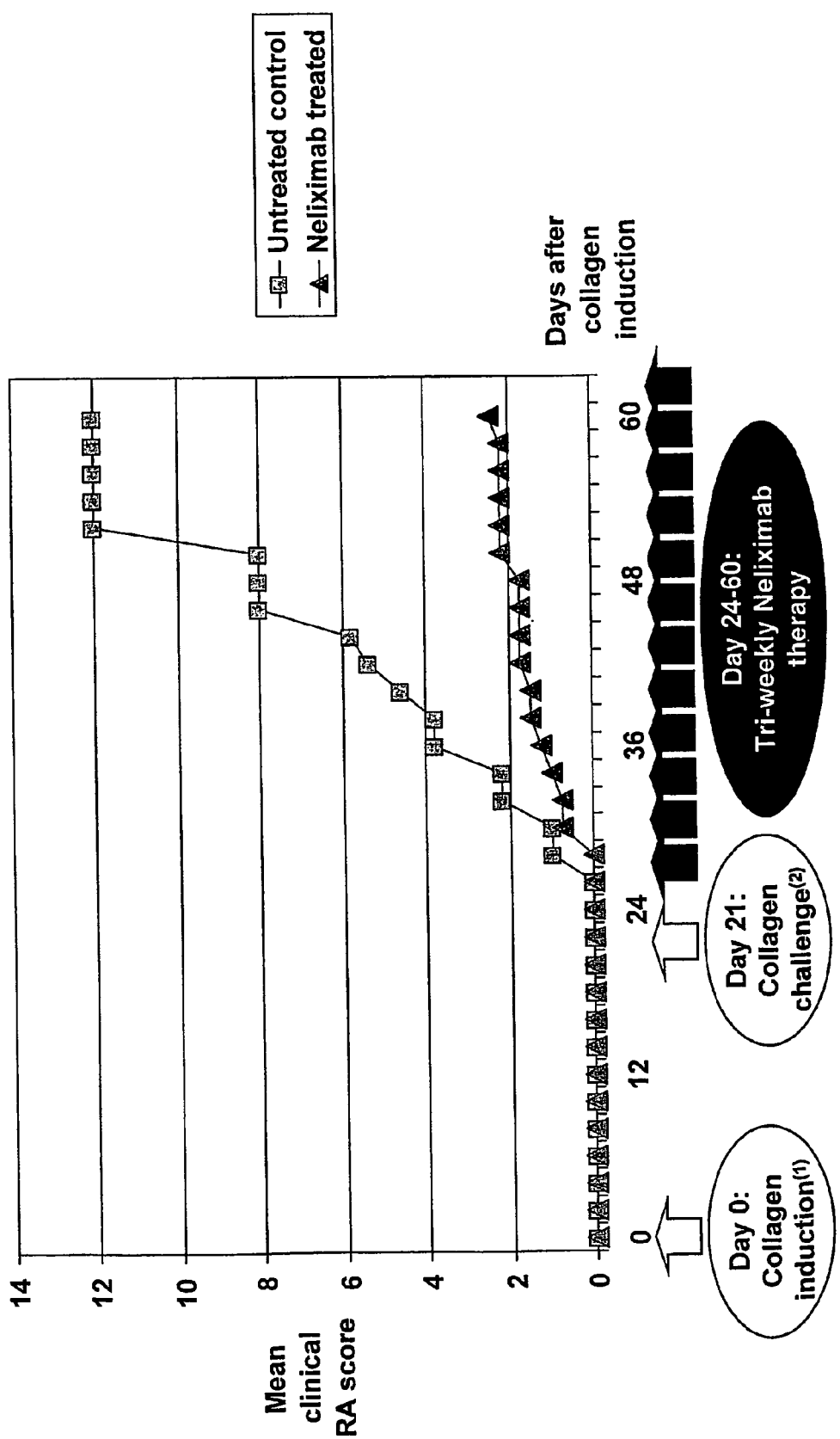

```
        10         20         30         40         50         60
         *          *          *          *          *          *
GAGGTCCAGCTGCAGCAGTCTGGACCGGAGCTGGTAAAGCCTGGGGCTTCAGTGAAGATG
CTCCAGGTCGACGTCGTCAGACCTGGCCTCGACCATTTCGGACCCCGAAGTCACTTCTAC
 E   V   Q   L   Q   Q   S   G   P   E   L   V   K   P   G   A   S   V   K   M>

70         80         90        100        110        120
         *          *          *          *          *          *
TCCTGCAAGGCTTCTGGGTACACTTTCACTACCTATGTTATGCACTGGGTGAAGCAGAAG
AGGACGTTCCGAAGACCCATGTGAAAGTGATGGATACAATACGTGACCCACTTCGTCTTC
 S   C   K   A   S   G   Y   T   F   T   T   Y   V   M   H   W   V   K   Q   K>
                                         ─── ─── ─── ─── ───

130        140        150        160        170        180
         *          *          *          *          *          *
CCTGGGCAGGGCCTTGAGTGGATTGGATATATTAATCCTTACAATGATGGTACTAACTAC
GGACCCGTCCCGGAACTCACCTAACCTATATAATTAGGAATGTTACTACCATGATTGATG
 P   G   Q   G   L   E   W   I   G   Y   I   N   P   Y   N   D   G   T   N   Y>
                                     ─── ─── ─── ─── ─── ─── ─── ─── ─── ───

190        200        210        220        230        240
         *          *          *          *          *          *
AATGAGAAGTTCAAAGGCAAGGCCACACTGACCTCAGACAAATCCTCCAGTACAGCCTAC
TTACTCTTCAAGTTTCCGTTCCGGTGTGACTGGAGTCTGTTTAGGAGGTCATGTCGGATG
 N   E   K   F   K   G   K   A   T   L   T   S   D   K   S   S   S   T   A   Y>
 ─── ─── ─── ─── ───

250        260        270        280        290        300
         *          *          *          *          *          *
ATGGAGCTCAGCACCCTGACCTCTGAGGACTCTGCGGTCTATTACTGTGCGGAATTTATT
TACCTCGAGTCGTGGGACTGGAGACTCCTGAGACGCCAGATAATGACACGCCTTAAATAA
 M   E   L   S   T   L   T   S   E   D   S   A   V   Y   Y   C   A   E   F   I>
                                                             ─── ───

310        320        330        340        350        360
         *          *          *          *          *          *
ACTAAGACAGTCGGTGGGTCCAACTGGTACCTCGATGTCTGGGGCGCAGGGACCACGGTC
TGATTCTGTCAGCCACCCAGGTTGACCATGGAGCTACAGACCCCGCGTCCCTGGTGCCAG
 T   K   T   V   G   G   S   N   W   Y   L   D   V   W   G   A   G   T   T   V>
 ─── ─── ─── ─── ─── ─── ─── ─── ─── ─── ─── ───

370        380        390
         *          *          *
ACCGTCTCCTCAGCCAAAACGACACCCCCAAAGCTT
TGGCAGAGGAGTCGGTTTTGCTGTGGGGGTTTCGAA
 T   V   S   S   A   K   T   T   P   P   K   L>
```

Figure 1

```
        10         20         30         40         50         60
         *          *          *          *          *          *
CAAATTGTTCTCACCCAGTCTCCAGCAATCATGTCTGCTTCTCCAGGGGAGAAGGTCACC
GTTTAACAAGAGTGGGTCAGAGGTCGTTAGTACAGACGAAGAGGTCCCCTCTTCCAGTGG
  Q  I  V  L  T  Q  S  P  A  I  M  S  A  S  P  G  E  K  V  T>

70         80         90        100        110        120
         *          *          *          *          *          *
ATGACCTGCAGTGCCAGCTCAAGTATAAGTTACATACACTGGTTCCAACAGAAGCCAGGC
TACTGGACGTCACGGTCGAGTTCATATTCAATGTATGTGACCAAGGTTGTCTTCGGTCCG
  M  T  C  S  A  S  S  S  I  S  Y  I  H  W  F  Q  Q  K  P  G>
             ─────────────────────────

130        140        150        160        170        180
         *          *          *          *          *          *
ACCTCCCCCAAAAGATGGATTTATGACACATCCAAACTGCCTTCTGGAGTCCCTGCTCGC
TGGAGGGGGTTTTCTACCTAAATACTGTGTAGGTTTGACGGAAGACCTCAGGGACGAGCG
  T  S  P  K  R  W  I  Y  D  T  S  K  L  P  S  G  V  P  A  R>
                            ───────────────

190        200        210        220        230        240
         *          *          *          *          *          *
TTCAGTGGCAGTGGGTCTGGGACCTCTTATTCTCTCACAATCAGCAGCATGGAGGCTGAA
AAGTCACCGTCACCCAGACCCTGGAGAATAAGAGAGTGTTAGTCGTCGTACCTCCGACTT
  F  S  G  S  G  S  G  T  S  Y  S  L  T  I  S  S  M  E  A  E>

250        260        270        280        290        300
         *          *          *          *          *          *
GATGCTGCCACTTATTACTGCCATCAGCGGAGTAGTTACACGTGGACGTTCGGTGGAGGC
CTACGACGGTGAATAATGACGGTAGTCGCCTCATCAATGTGCACCTGCAAGCCACCTCCG
  D  A  A  T  Y  Y  C  H  Q  R  S  S  Y  T  W  T  F  G  G  G>
                            ─────────────────

310        320        330        340        350
         *          *          *          *          *
ACCAAGCTGGAAATCAAACGGGCTGATGCTGCACCAACTGTATCCGCGGCCGC
TGGTTCGACCTTTAGTTTGCCCGACTACGACGTGGTTGACATAGGCGCCGGCG
  T  K  L  E  I  K  R  A  D  A  A  P  T  V  S  A  A  A>
```

Figure 2

```
          10        20        30        40        50        60
           *         *         *         *         *         *
CAGGTGCAGCTGAAGCAGTCTGGACCGGAGCTGGTAAAGCCTGGGGCTTCAGTGAAGATG
GTCCACGTCGACTTCGTCAGACCTGGCCTCGACCATTTCGGACCCCGAAGTCACTTCTAC
 Q   V   Q   L   K   Q   S   G   P   E   L   V   K   P   G   A   S   V   K   M>

70        80        90       100       110       120
           *         *         *         *         *         *
TCCTGCAAGGCTTCTGGGTACACTTTCACTACCTATGTTATGCACTGGGTGAAGCAGAAG
AGGACGTTCCGAAGACCCATGTGAAAGTGATGGATACAATACGTGACCCACTTCGTCTTC
 S   C   K   A   S   G   Y   T   F   T   T   Y   V   M   H   W   V   K   Q   K>
                                          ─── ─── ─── ─── ───

130       140       150       160       170       180
           *         *         *         *         *         *
CCTGGGCAGGGCCTTGAGTGGATTGGATATATTAATCCTTACAATGATGGTACTAACTAC
GGACCCGTCCCGGAACTCACCTAACCTATATAATTAGGAATGTTACTACCATGATTGATG
 P   G   Q   G   L   E   W   I   G   Y   I   N   P   Y   N   D   G   T   N   Y>
                                      ─── ─── ─── ─── ─── ─── ─── ─── ─── ───

190       200       210       220       230       240
           *         *         *         *         *         *
AATGAGAAGTTCAAAGGCAAGGCCACACTGACCTCAGACAAATCCTCCAGTACAGCCTAC
TTACTCTTCAAGTTTCCGTTCCGGTGTGACTGGAGTCTGTTTAGGAGGTCATGTCGGATG
 N   E   K   F   K   G   K   A   T   L   T   S   D   K   S   S   S   T   A   Y>
 ─── ─── ─── ─── ─── ───

250       260       270       280       290       300
           *         *         *         *         *         *
ATGGAGCTCAGCACCCTGACCTCTGAGGACTCTGCGGTCTATTACTGTGCGGAATTTATT
TACCTCGAGTCGTGGGACTGGAGACTCCTGAGACGCCAGATAATGACACGCCTTAAATAA
 M   E   L   S   T   L   T   S   E   D   S   A   V   Y   Y   C   A   E   F   I>
                                                              ─── ───

310       320       330       340       350       360
           *         *         *         *         *         *
ACTAAGACAGTCGGTGGGTCCAACTGGTACCTCGATGTCTGGGGCGCAGGGACCACGGTC
TGATTCTGTCAGCCACCCAGGTTGACCATGGAGCTACAGACCCCGCGTCCCTGGTGCCAG
 T   K   T   V   G   G   S   N   W   Y   L   D   V   W   G   A   G   T   T   V>
 ─── ─── ─── ─── ─── ─── ─── ─── ─── ─── ─── ───

370
           *
ACCGTCTCCTCA
TGGCAGAGGAGT
 T   V   S   S>
```

Figure 9

```
         10        20        30        40        50        60
          *         *         *         *         *         *
GATATTGTGCTAACTCAGTCTCCAGCAATCATGTCTGCTTCTCCAGGGGAGAAGGTCACC
CTATAACACGATTGAGTCAGAGGTCGTTAGTACAGACGAAGAGGTCCCCTCTTCCAGTGG
  D  I  V  L  T  Q  S  P  A  I  M  S  A  S  P  G  E  K  V  T>

70        80        90       100       110       120
          *         *         *         *         *         *
ATGACCTGCAGTGCCAGCTCAAGTATAAGTTACATACACTGGTTCCAACAGAAGCCAGGC
TACTGGACGTCACGGTCGAGTTCATATTCAATGTATGTGACCAAGGTTGTCTTCGGTCCG
  M  T  C  S  A  S  S  S  I  S  Y  I  H  W  F  Q  Q  K  P  G>
              ‾  ‾  ‾  ‾  ‾  ‾  ‾  ‾  ‾  ‾

130       140       150       160       170       180
          *         *         *         *         *         *
ACCTCCCCCAAAAGATGGATTTATGACACATCCAAACTGCCTTCTGGAGTCCCTGCTCGC
TGGAGGGGGTTTTCTACCTAAATACTGTGTAGGTTTGACGGAAGACCTCAGGGACGAGCG
  T  S  P  K  R  W  I  Y  D  T  S  K  L  P  S  G  V  P  A  R>
                          ‾  ‾  ‾  ‾  ‾  ‾  ‾

190       200       210       220       230       240
          *         *         *         *         *         *
TTCAGTGGCAGTGGGTCTGGGACCTCTTATTCTCTCACAATCAGCAGCATGGAGGCTGAA
AAGTCACCGTCACCCAGACCCTGGAGAATAAGAGAGTGTTAGTCGTCGTACCTCCGACTT
  F  S  G  S  G  S  G  T  S  Y  S  L  T  I  S  S  M  E  A  E>

250       260       270       280       290       300
          *         *         *         *         *         *
GATGCTGCCACTTATTACTGCCATCAGCGGAGTAGTTACACGTGGACGTTCGGTGGAGGC
CTACGACGGTGAATAATGACGGTAGTCGCCTCATCAATGTGCACCTGCAAGCCACCTCCG
  D  A  A  T  Y  Y  C  H  Q  R  S  S  Y  T  W  F  G  G  G>
                          ‾  ‾  ‾  ‾  ‾  ‾  ‾

310
          *
ACCAAGCTGGAAATCAAA
TGGTTCGACCTTTAGTTT
  T  K  L  E  I  K>
```

Figure 10

ANTI-TIRC7 ANTIBODIES IN THERAPY OF INFLAMMATORY DISEASES

FIELD OF THE INVENTION

This application is a §371 national stage of PCT International Application No. PCT/EP02/14733, filed Dec. 23, 2002, claiming priority of European Patent Application No. 01 130 730.3, filed Dec. 21, 2001; European Patent Application No. 02 013 261.9, filed Jun. 17, 2002; and European Patent Application No. 02 018 809.0, filed Aug. 22, 2002 the contents of all of which are hereby incorporated by reference.

The present invention generally relates to compositions and advantageous uses thereof in the treatment of inflammatory diseases, in particular arthritis.

In one aspect, the present invention relates to the use of T-cell immune response cDNA7 (TIRC7) antagonist, preferably anti-TIRC7 antibody, for the preparation of a pharmaceutical composition for preventing or treatment of a mammal subject afflicted with an inflammatory disease, in particular arthritis, wherein said pharmaceutical composition is in a form adapted for particular therapeutic and preventive treatment regimens.

In a further aspect, the present invention relates to a particular monoclonal anti-TIRC7 antibody which in mice has been shown to be efficacious in the treatment and prevention of rheumatoid arthritis and that is capable of prolonging cardiac allograft survival, and to chimeric, humanized, and fully human versions of said antibody.

Furthermore, the current invention pertains to the discovery that combination therapy, involving the use of TIRC7 antagonist, preferably anti-TIRC7 antibody in conjunction with an anti-inflammatory drug, preferably TNF-α antagonist, produces markedly superior results compared to the use of each agent alone in the treatment of an inflammatory disease, particularly in rheumatoid arthritis. Hence, the present invention relates to the use of TIRC7 antagonist for the preparation of pharmaceutical compositions for the treatment or prevention of an inflammatory disease for patients receiving previously, concomitantly or subsequently a medicament comprising an anti-inflammatory drug, and vice versa.

Several documents are cited throughout the text of this specification. Each of the documents cited herein (including any manufacturer's specifications, instructions, etc.) are hereby incorporated herein by reference; however, there is no admission that any document cited is indeed prior art as to the present invention

BACKGROUND OF THE INVENTION

Rheumatoid arthritis (RA) is estimated to occur in one to three percent of the general population and is one of the most common causes of disability. There is no known cure for rheumatoid arthritis and current disease modifying antirheumatic drugs (DMARDs) fail to address the underlying cause of the disease. Current rheumatoid arthritis treatment consists predominantly of symptomatic relief by administration of non-steroidal anti-inflammatory drugs (NSAIDs). NSAID treatment is mainly effective in the early stages of rheumatoid arthritis, and is unlikely to produce suppression of joint inflammation if the disease is present for more than one year.

Gold, methotrexate, immunosuppressants and corticosteroids have been tried with limited success. In advanced cases of rheumatoid arthritis, the traditional methods of treatment have generally been aimed at avoiding toxicity.

Disease modifying antirheumatic drugs also play a predominant role in the treatment of rheumatoid arthritis, but their toxicological profile limits their application and effectiveness in long-term therapy. For example, methotrexate (MTX) has demonstrated long-term efficacy, but its toxicological profile, e.g., gastrointestinal upset, mucosal ulcerations, renal impairment, pulmonary toxicity, is the most common reason cited among patients for treatment termination. The toxicity profile of MTX remains a major concern among physicians and prolonged treatment with MTX may require invasive biopsy procedures in a patient to monitor hepatic function. Another disease modifying antirheumatic drug, sulfasalazine, has been shown to be more effective than hydroxychloroquine in the treatment of rheumatoid arthritis, but it is not as well tolerated, with 20% of patients terminating treatment due to adverse gastrointestinal side effects. Azathioprine, penicillamine and gold compounds have also been shown to be efficacious in treating rheumatoid arthritis, but are not as well tolerated as MTX, sulfasalazine or hydroxychloroquine. Cylcosporine has shown applicability in treating rheumatoid arthritis, but its renal toxicity has limited its usage to salvage therapy or in combination therapy with other disease modifying antirheumatic drugs. Thus, treating rheumatoid arthritis with disease modifying antirheumatic drugs remains complicated by poor efficacy and the occurrence of adverse side effects. Lack of predictability of these adverse reactions has made regular monitoring of a patients physiological condition mandatory where long term therapy is anticipated. Such monitoring include, for example, measuring blood count, and/or performing liver, kidney, urine or ophthalmologic tests.

Historically, treatment of the inflammatory actions was available through the use of non-steroidal anti-inflammatory drugs (NSAIDs). This class of drugs possesses anti-inflammatory, analgesic and anti-pyretic activity, and are widely used to treat chronic inflammatory states such as arthritis. However, common NSAIDs that are active in reducing the PG-induced pain and swelling associated with the inflammation process are also active in affecting the other PG-roles which is not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved. Prostaglandins (PGs) play a major role in the inflammation process and the inhibition of prostaglandin production, especially production of PGG2, PGH2 and PGE2, has been a common target of anti-inflammatory drug discovery. Along with this role, PGs play a cytoprotective role in the gastrointestinal tract and also on renal function. Previous NSAIDs have been found to prevent the production of PGs by inhibiting enzymes in the human arachidonic acid/prostaglandin pathway, including the enzyme cyclooxygenase (COX).

Cytokines are signaling peptide molecules that modulate a wide variety of cellular functions that includes inflammation. Cellular response occurs as a result of interaction between a particular cytokine and high-affinity cell-surface receptors specific for each cytokine. The receptor-binding event leads to the transduction of a signal across the cell membrane and the activation of intracellular biochemical pathways and gene translation or transcription events. Tumor Necrosis Factor-alpha (TNF-α) is a cytokine produced primarily by activated monocytes and macrophages. Excessive or unregulated tumor necrosis factor production has been implicated in mediating a number of diseases. Recent studies indicate that tumor necrosis factor has a causative role in the pathogenesis of rheumatoid arthritis. Additional studies demonstrate that inhibition of tumor necrosis factor has broad application in the treatment of inflammation, inflammatory bowel disease, multiple sclerosis and asthma.

Interleukin-8 (IL-8) is another pro-inflammatory cytokine, which is produced by mononuclear cells, fibroblasts, endothelial cells, and keratinocytes, and is associated with conditions including inflammation.

Interleukin-1 (IL-1) is produced by activated monocytes and macrophages and is also involved in the inflammatory response. IL-1 plays a role in many pathophysiological responses including rheumatoid arthritis, fever and reduction of bone resorption.

Rau et al., J. Rheumatol. 25 (1998), 1485-1492, describe a combination of methotrexate (MTX) and parenteral gold or MTX and other disease modifying antirheumatic drugs (DMARD) in the treatment of rheumatoid arthritis. Conagham and Brooks, Curr. Opin. Rheumatol. 8 (1996), 176-182, describe methotrexate in combination therapy with intramuscular gold and other DMARDs for the treatment of arthritis. Fürst, J. Rheumtol., Suppl. 44 (1996) Rheumatoid Arthritis: The Status and Future of Combination Therapy, 86-90, reviews 16 references and describes an approach to rheumatoid arthritis disease modifying drug combination therapy. Li, Curr. Opin, Rheumatol. 10 (1998), 159-168, describes certain disease modifying anti-rheumatic drugs in combination therapy in patients suffering from rheumatoid arthritis. Conagham et al., Curr. Opin. Rheumatol. 9 (1997), 183-190, describes MTX, sulfasalazine, and hydroxychloroquine in combination therapy for the treatment of rheumatoid arthritis. O'Dell et al., J. Rheumatol. Suppl. 44 (1996) Rheumatoid Arthritis: The Status and Future of Combination Therapy, 72-74, describe the single agent therapy of MTX, sulfasalazine or hydroxychloroquine and the combination of MIX, sulfasalazine and hydroxychloroquine, and MTX in combination with either sulfasalazine or hydroxychloroquine. Dijkmans et al., J. Rheumatol. Suppl. 44 (1996), 61-63, describes a 2 phase study using a combination of cyclosporin A (CsA) (an inhibitor of interleukin 2 (IL-2) and other cytokine production) with chloroquine for the treatment of rheumatoid arthritis.

The state of the art as regards several approaches for the treatment of inflammatory diseases is summarized in WO01/00229, which in addition describes combinations of a tumor necrosis factor antagonizing agent and a cyclooxygenase-2 inhibiting agent for treating inflammatory disease in a mammal.

Despite these and other advances, a great need remains for better therapies for inflammatory disease, in particular for rheumatoid arthritis. The solution to said technical problem is achieved by providing the embodiments characterized in the claims, and described further below.

DESCRIPTION OF THE INVENTION

In one aspect the present invention relates to the use of T-cell immune response cDNA 7 (TIRC7) antagonist for the preparation of a pharmaceutical composition for preventing or treatment of a mammal subject afflicted with an inflammatory disease, wherein said pharmaceutical composition is in a form adapted for administration wherein
  (a) said administration of TIRC7 antagonist to the patient is in a dosage which is in the range of from about 0.5 mg/kg/day to about 50 mg/kg/day and wherein said administration is at intervals of one to three times a week during a period of at least two weeks for a therapeutic treatment regimen and at daily intervals over a week for a preventive treatment regimen;
  (b) said therapeutic treatment regimen and preventive treatment regimen may be combined and/or repeated at one or several intervals.

The term "TIRC7" as used in accordance with the present invention, denotes a protein which initially has been described to be involved in the signal transduction of T-cell activation and proliferation and that, preferably in a soluble form is capable of inhibiting or suppressing T-cell proliferation in response to alloactivation in a mixed lymphocyte culture or in response to mitogens when exogeneously added to the culture. In vitro translated TIRC7 protein has been shown to be able to efficiently suppress in a dose dependent manner the proliferation of T-cells in response to alloactivation in a mixed lymphocyte culture or in response to mitogens. TIRC7 is known to the person skilled in the art and described, inter alia, in WO99/11782, Utku, Immunity 9 (1998), 509-518 and Heinemann, Genomics 57 (1999), 398-406, which also disclose the amino and nucleic acid sequences of TIRC7.

The terms "antagonist" and "inhibitor" are used interchangeably herein and in accordance with the present invention include chemical agents that modulate the action of TIRC7, either through altering its enzymatic or biological activity or through modulation of expression, e.g., by affecting transcription or translation. In some cases the antagonist may also be a substrate or ligand binding molecule. The term "inhibitor" includes both substances which reduce the activity of the target protein, here TIRC7, and those which nullify it altogether. When more than one possible activity is defined herein for a protein, the inhibitor may modulate any or all of its activities. An "antagonist" that modulates the activity of TIRC7 and causes for example a response in a cell based assay refers to a compound that alters directly or indirectly the activity of a protein or the amount of active protein. Typically, the effect of a TIRC7 antagonist is substantially the same as that of the anti-TIRC7 antibodies described in Utku, Immunity 9 (1998), 509-518. Antagonists include competitive as well as non-competitive antagonists. A competitive antagonist (or competitive blocker) interacts with or near the site specific for agonist binding. A non-competitive antagonist or blocker inactivates the function of the receptor by interacting with a site other than the agonist interaction site. Preferably, the antagonist/inhibitor of TIRC7 are small chemical agents which directly interact with TIRC7. Therefore, there will preferably be a direct relationship between the molar amount of compound required to inhibit or stimulate TIRC7 activity and the molar amount of TIRC7 present or lacking in the cell. Furthermore, the TIRC7 antagonist has preferably at least one of the, more preferably the same biological activities as Neliximab regarding TNF-α, IL-2, IL-4, IL-6, IL-10, IFN-γ expression and proliferation of lymphocytes in response to mitogen; see the examples and Figures.

TIRC7 antagonists may be peptides, proteins, nucleic acids, a TIRC7 gene targeting vector, antibodies, small organic compounds, peptide mimics, aptamers or PNAs (Milner, Nature Medicine 1 (1995), 879-880; Hupp, Cell 83 (1995), 237-245; Gibbs, Cell 79 (1994), 193-198; Gold, Ann. Rev. Biochem. 64 (1995), 736-797). For the preparation and application of such compounds, the person skilled in the art can use the methods known in the art, for example those referred to above. Furthermore, antagonists/inhibitors of TIRC7 and methods for obtaining the same are described in, for example, WO02/36149.

As used herein, the term "mammal" means any member of the higher vertebrate animals included in the class Mammalia, as defined in Webster's Medical Desk Dictionary 407 (1986), and includes but is not limited to humans, other primates, pigs, dogs, and rodents (such as immune suppressed mice). In the preferred embodiment of this invention, the mammal is a human.

The instant composition of matter can be of any form known in the art. In one embodiment, the composition comprises a pharmaceutically acceptable carrier and one or more discrete pharmaceutical compounds that function as the agent that specifically alters TIRC7 expression and/or activity. In another embodiment, the composition of matter comprises a naturally-occurring composition, or an extract or component thereof, which is deemed pharmaceutically or cosmetically acceptable. Such naturally occurring compositions contain certain components which function as active agents, and numerous others that serve as pharmaceutical or cosmetically carriers. The instant compositions can be artificial, naturally occurring, or a combination thereof. In addition, the compositions can be of any physical form known in the art, such as liquids (e.g., solutions, creams, lotions, gels, injectables), solids (e.g., tablets, capsules, powders, granules), aerosols, and coatings. For therapeutic use, TIRC7 antagonist is administered to a patient, preferably a human, for treatment of an inflammation disorder, for example arthritis. Thus, for example, TIRC7 antagonist compositions can be administered by parental administration, for example, intravenous injection, subcutaneous injection, intramuscular injection, or intramedullary injection. Other routes of administration include, for example, intraarticular, intraperitoneal or subcutaneous routes by bolus injection, continuous infusion, sustained release from implants, or other suitable techniques. Typically, TIRC7 antagonist therapeutic agent will be administered in the form of a composition comprising purified protein in conjunction with physiologically acceptable carriers, excipients or diluents. Such carriers will be non-toxic to recipients at the dosages and concentrations employed. Ordinarily, the preparation of such compositions entails combining the TIRC7 antagonist with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product is formulated as a lyophilisate using appropriate excipient solutions (e.g., sucrose) as diluents. Appropriate dosages can be determined in trials.

In accordance with appropriate industry standards, preservatives may also be added, such as benzyl alcohol. The amount and frequency of administration will depend, of course, on such factors as the nature and severity of the indication being treated, the desired response, the condition of the patient, and so forth. It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration. Treatment dosages generally may be titrated to optimize safety and efficacy.

By devising alternative schedules and dosages, it has been discovered in accordance with the present invention that effective treatment regimens for TIRC7 antagonist, in particular anti-TIRC7 antibody in the treatment of inflammatory diseases, in particular arthritis, do exist. This has been exemplified with a murine anti-TIRC7 antibody (see Example 1) in an RA mice model; see Examples 5 to 9. A chimeric (murine/human) version of this antibody has been produced, designated Neliximab, (see Example 2) and could be shown to have substantially the same antigen binding affinity and biological activity; see Examples 2 and 4, Tables 5 and 6. Accordingly, it is reasonable to expect that the results obtained for the murine anti-TIRC7 antibody in mice are transferable to the chimeric anti-TIRC7 antibody as well as to humanized and fully human versions thereof in the treatment of inflammatory diseases, in particular rheumatoid arthritis, in humans. The chimeric version of the mentioned anti-TIRC7 antibody has been designated "Neliximab" and the original monoclonal antibody is indicated with "murine" Neliximab. Those antibodies are further described below.

With respect to the dosage indication, i.e. the range of from about 0.5 mg/kg/day to about 50 mg/kg/day TIRC7 antagonist, it is to be understood that this dosage refers to the dosage for anti-TIRC7 antibody Neliximab described in the examples and which is expected to be therapeutically effective at those concentrations. Put in other words, a TIRC7 antagonist with similar molecular weight and biological activity as Neliximab, for example another anti-TIRC7 antibody, may be used at the mentioned concentrations. On the other hand, a TIRC7 antagonist which is, for example, only a fifth in molecular weight but twice as biologically active as Neliximab correspondingly may be used at a tenth of said concentration, i.e. in the range of 0.05 mg/kg/day to 5 mg/kg/day. Hence, the person skilled in the art knows how to sensibly construe the mentioned dosage for any given TIRC7 antagonist. Typically, dosage-effect relationships from studies in animal models may be used for guidance regarding effective dosages for treatment of rheumatoid arthritis in accordance with the present invention. In terms of treatment protocols, it should be appreciated that the dosage to be administered will depend on several factors, including the particular agent that is administered, the route administered, the condition of the particular patient, etc. It will generally be desirable to administer the TIRC7 antagonist either parenterally, intravenously, or subcutaneously. Other routes of administration are also contemplated, including intranasal and transdermal routes, and by inhalation. When administered, the therapeutic composition for use in this invention is preferably in the form of a pyrogen-free, intravenously, or subcutaneously-acceptable aqueous solution. The preparation of such a protein solution, having due regard to pH, isotonicity, stability and the like, is within the skill of the art. However, administration by other routes is contemplated where appropriate. Generally speaking, one will desire to administer an amount of the agent that is effective to achieve a serum level commensurate with the concentrations found to be effective in the animal model. Thus, where an agent is found to demonstrate in activity at, e.g., 10 µM in the animal model, one will desire to administer an amount of the drug that is effective to provide about a 10 µM concentration in a human patient. Determination of these parameters is well within the skill of the art. Any TIRC7 antagonist may be tested for a corresponding appropriate dosage regimen in the RA mice model described in the examples, optionally with Neliximab or a corresponding anti-TIRC7 antibody as a positive control. Thus, in accordance with dosage relationships of a therapeutic agent in animal models such as mice versus human known for, e.g., Enbrel, it is possible to estimate the appropriate dosage for a TIRC7 antagonist tested in the RA mice model described in the examples. Accordingly, in one embodiment, it is preferred to use a dosage regimen in a human patient, which corresponds to one of those of Neliximab in the described RA mice model. Preferably, the dosage is in the range of about 5 mg/kg/day to about 30 mg/kg/day. More preferably, the dosage is in the range of about 25 mg/kg/day.

Generally, administration frequency comprise daily administration, interval therapy (1, 2-3 times/week) with therapy duration of a single administration, interval therapy over limited time period (weeks up to months) and repeated interval therapy, as long as dosage and treatment regimen as defined herein are followed; see also the treatment regimens shown in FIGS. 3 to 7. Thus, in a preferred embodiment, the treatment regimen comprises a daily administration for about a week, followed by an interval therapy of 2-, preferably 3-times/week for 17 days, which may be prolonged to 3 or 4 weeks. For a continuous treatment, an interval therapy of 2-, preferably 3-times/week for one month may preferably be used, which may be repeated one or more times. Before, in between or after a therapeutic treatment regimen, a preventive treatment regimen may be included, preferably in situations where the patient envisages or suffers from a sudden increase or onset of the disease. Said preventive treatment regimen preferably comprises a daily administration of TIRC7 antagonist for about week at higher doses. Those preventive treatment regimen are also preferably used, either alone or in combination with a therapeutic one, for the treatment of cardiac allograft rejection.

Figure 6:
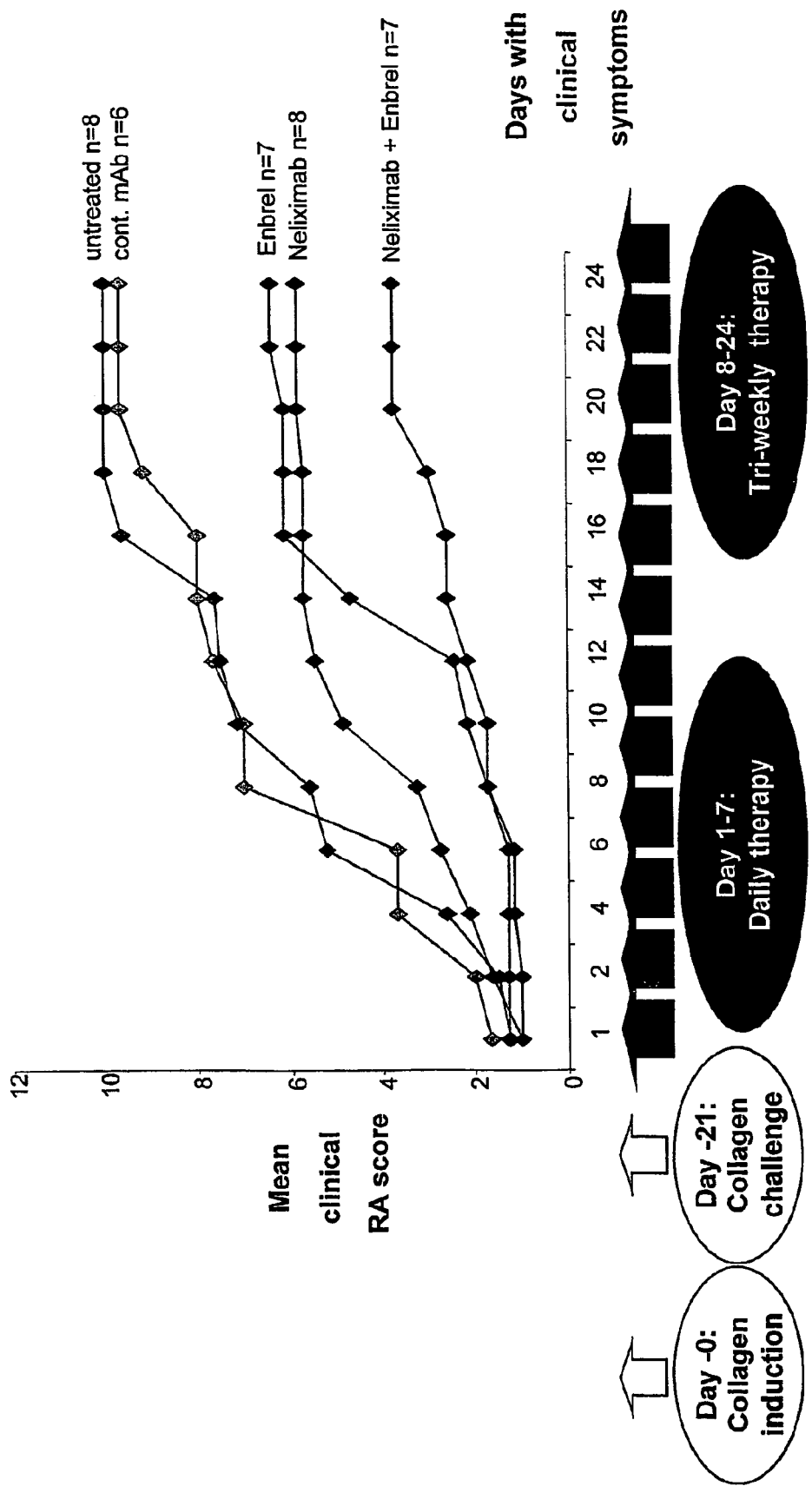

In addition, or alternatively, a treatment regimen may be followed that has been established for other anti-inflammatory drugs, preferably for Enbrel or Remicade. For example, a recommended dose for JRA patients is 0.4 mg/kg (maximum dose, 25 mg) twice weekly by subcutaneous injection 72-96 hours apart. In a preferred embodiment, said therapeutic treatment regimen for the pharmaceutical composition of the invention is preceded by a preventive treatment regimen. Such treatment regimen is shown in FIG. 6. A preventive treatment regimen comprising a daily treatment for week may be used, for example, before full onset of the disease while first symptoms or a predisposition have been diagnosed.

Recommended dose for treatment of rheumatoid arthritis and psoriatic arthritis in adults is 25 mg twice weekly by subcutaneous injection 72-96 hours apart.

The methods, combinations and compositions of the present invention can be useful for the treatment or prevention of inflammatory and arthritic disorders in a mammal including, but not limited to, disorders such as rheumatoid arthritis (RA); osteoarthritis (OA); spondylarthropy; ankylosing spondylitis; psoriatic arthritis; reactive arthritis; IBD related arthritis; undifferentiated spondyloarthropathy; Reider's syndrome; systemic lupus erythematosus; Behcet's disease; eosinophilia fasciitis; eosinophila-myalgia syndrome; familial Mediterranean fever; hereditary angioedema; juvenile chronic arthritis; palindromic rheumatism; idiopathic polymyositis; dermatomyositis; inclusion body myositis; systemic sclerosis; atherosclerosis; sarcoidisis; Reynaud's phenomenon; Sjogren's syndrome; Still's disease; systemic rheumatoid vasculitis; vasculitis; Wegener's granulomatosis; Whipple's disease; and xerostomia.

In a preferred embodiment, said inflammatory disease is rheumatoid arthritis.

As demonstrated in the examples, anti-TIRC7 antibodies have been shown to be efficacious in the treatment of arthritis. Accordingly, the TIRC7 antagonist to be used in accordance with the present invention is preferably an anti-TIRC7 antibody or fragment thereof. Such antibodies are described for example in WO99/11782 and Utku, Immunity 9 (1998), 509-518. Preferably, said antibody is a human chimeric, humanized or fully human antibody, for example in order to avoid HAMA response in a human subject; see also infra The chimeric antibodies can comprise portions derived from two different species (e.g., human constant region and murine variable or binding region). The portions derived from two different species can be joined together chemically by conventional techniques or can be prepared as single contiguous proteins using genetic engineering techniques. DNA encoding the proteins of both the light chain and heavy chain portions of the chimeric antibody can be expressed as contiguous proteins. In a particularly preferred embodiment said antibody is an antibody as described below, i.e. which is or is derived from Neliximab disclosed in the examples.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agents in the composition are the TIRC7 antagonist and optionally an anti-inflammatory drug such as one of those described further below. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use. In particular, it comprises instructions for administration of said an TIRC7 antagonist composition to a patient suffering from an inflammatory disease, said instructions directing the administration of TIRC7 antagonist to the patient in a dosage and regimen as defined herein above.

In a preferred embodiment, the article of manufacture is for use in the treatment of arthritis and said TIRC7 antagonist is a TIRC7 antagonist as defined hereinabove.

In a further aspect, the present invention relates to an anti-TIRC7 antibody or binding fragment thereof comprising in its variable region at least one complementarity determining region (CDR) of the $V_H$ and/or $V_L$ of the variable region comprising the amino acid sequence depicted in FIG. 1 ($V_H$) (SEQ ID NO: 2) and FIG. 2 ($V_L$) (SEQ ID NO: 4) or depicted in FIG. 9 ($V_H$) (SEQ ID NO: 9) and FIG. 10 ($V_L$) (SEQ ID NO: 11).

The person skilled in the art knows that each variable domain (the heavy chain $V_H$ and light chain $V_L$) of an antibody comprises three hypervariable regions, sometimes called complementarity determining regions or "CDRs" flanked by four relatively conserved framework regions or "FRs". The CDRs contained in the variable regions of the antibody of the invention can be determined, e.g., according to Kabat, Sequences of Proteins of Immunological Interest (U.S. Department of Health and Human Services, third edition, 1983, fourth edition, 1987, fifth edition 1990). The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art will readily appreciate that using the variable domains or CDRs described herein antibodies can be constructed according to methods known in the art, e.g., as described in EP-A1 0 451 216 and EP-A1 0 549 581. Furthermore, the person skilled in the art knows that binding affinity may be enhanced by making amino acid substitutions within the CDRs or within the hypervariable loops (Chothia and Lesk, J. Mol. Biol. 196 (1987), 901-917) which partially overlap with the CDRs as defined by Kabat. Thus, the present invention also relates to antibodies wherein one or more of the mentioned CDRs comprise one or more, preferably not more than two amino acid substitutions. Preferably, the antibody of the invention comprises in one or both of its immunoglobulin chains two or all three CDRs of the above mentioned variable regions shown in FIGS. 1 and 2, and FIGS. 9 and 10, respectively.

As described in the examples, the antibody of the invention recognizes a fragment of the amino acid sequence from T cell immune response cDNA 7 (TIRC7) protein (peptide 7c: DLPDASVNGWSSDEEKAGGLDDEE, SEQ ID NO: 5). More particularly, the antibody of the present invention and binding fragment thereof recognizes the amino acid sequence DLPDASVNGWSSDE (peptide 6, SEQ ID NO: 6). TIRC7 is known to the person skilled in the art and described, inter alia, in WO99/11782, Utku, Immunity 9 (1998), 509-518 and Heinemann, Genomics 57 (1999), 398-406, which also disclose the amino and nucleic acid sequences of TIRC7.

As it was shown by Utku et al. (Immunity, 1998), polyclonal antibodies against TIRC7 suppressed the proliferation of activated T-cells in MLR in a dose dependent manner. While these promising results suggested the therapeutic use of such antibodies, there was a need for antibodies that have high binding specificity and affinity, and that efficiently suppress, for example, T cell proliferation thereby allowing the use of such antibodies at low doses in order to circumvent possible HAMA responses in a subject. Furthermore, such antibodies may have different or differently pronounced effects on, e.g., cytokine production which can be important in the treatment of certain immune response related diseases, for example inflammatory diseases.

In order to find antibodies which supply the needs mentioned above, mice were immunized with peptides from several domains of TIRC7, which were thought to represent putatively appropriate antigens; see FIG. 1 of WO99/11782. However, while most of these peptides proofed to be good antigens for raising polyclonal antibodies, several attempts failed to produce stable hybridomas which secreted antibodies with the desired binding affinity and/or biological activity. However, with three of six peptides derived from the sequence of several hypothetically extracellular domains of TIRC7, the inventors eventually succeeded with generating stable hybridomas producing the desired monoclonal antibodies. Thus, 192 stable antibody producing hybridomas were received and 42 antibodies were tested from those antibodies 15 antibodies were selected which inhibited cell proliferation as well as the secretion of IFNγ and IL-2 of PHA-stimulated human PBMC of healthy donors below 30% calculated in relation to the positive control (100%). Finally one antibody was selected, clone #17, descended from fusions performed with spleen cells of mice that had been immunized with peptides derived from the largest extracellular loop of TIRC7. In accordance with the present invention, it could then surprisingly be shown that chimeric recombinant antibodies comprising the $V_H$- and $V_L$-variable regions of the murine monoclonal antibodies and either the human gamma or kappa constant region exhibit substantially the same specificity, binding affinity and biological activity as the murine donor antibodies. Since it could be shown that a murine version of this antibody, called "murine Neliximab", has preventive activity in rheumatic arthritis (see the examples), the same activity is expected for the chimeric mouse/human version thereof called "Neliximab" as well as for corresponding humanized and human antibodies.

Hence, the antibodies of the present invention are expected to be generally useful in the modulation of immune responses. Modulating the immune response, as for example by activating or inhibiting the proliferation and/or differentiation of T-cells, B-cells, NK cells, LAK cells, dendritic cells, monocytes, macrophages or other immune system cells, may be useful in treating autoimmune diseases, allergic diseases, and in transplantation therapies where graft vs. host or host vs. graft effects may be undesirable. The antibodies could also be immune stimulants in settings such as cancer, infectious disease, sepsis, wound healing, or immunization. Alternatively, they could be immune suppressants. They could also be used to detect inflammation, and preferably modulate inflammation by activating or inhibiting activation of immune or inflammatory cells. A preferred method involves detecting (and preferably modulating) inflammation in tissues such as inflamed vasculature or leukocytes. Furthermore, the antibodies of the present invention can be used to induce or maintain immune unresponsiveness. The term "immune unresponsiveness" comprises non-unresponsiveness of immune cell subsets like T-cell or B-cells, NK-cells, monocytes and/or macrophages.

The terms "treatment", "treating" and the like are used herein to generally mean obtaining a desired pharmacological and/or physiological effect The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

Furthermore, the term "subject" as employed herein relates to animals in need of amelioration, treatment and/or prevention of immunological diseases as disclosed herein. Most preferably said subject is a human.

Hence, the antibodies described herein can be used for any application described for anti-TIRC7 antibodies before, in particular if therapeutic and in vivo diagnostic uses are envisaged; see for example WO99/11782 and co-pending PCT application no. PCT/EP02/13384, the disclosure content of which is hereby incorporated by reference.

Without intending to be bound by theory, it is believed that the described anti-TIRC7 antibodies are capable of modulating the function (e.g., signaling or adhesive activities) of TIRC7, its family members and/or their ligands, for example by interfering with the interaction of TIRC7 with its ligand. However, irrespective the theory behind the molecular mechanism of action, the antibody of the invention can be characterized by (1) having binding affinity to TIRC7 in the order of at least $10^{-7}$M, preferably at least $10^{-8}$M, more preferably at least $0.5 \times 10^{-8}$M, still more preferably at least $10^{-8}$M, and most preferably at least $10^{-9}$M or $10^{-10}$M and (2) being capable of inhibiting proliferation of mitogen-stimulated PBMCs in an assay as described in Example 1.

Preferably, the antibody of the invention and any binding fragment derived thereof is capable of inhibiting the proliferation as well as the secretion of IFN-γ and IL-2 of PHA-stimulated human PBMC of healthy donors below 30% calculated in relation to the positive control (100%). Most preferably, the antibody or binding fragment is capable of inhibiting the proliferation of PHA-stimulated human PBMC of healthy donors below 25% or even below 20% or more calculated in relation to the positive control (100%).

Thus the present antibodies are preferably capable of modulating, preferably inhibiting proliferation of peripheral blood mononuclear cells (PBMCs). Preferably, the antibodies of the present invention modulate at least one of the following (which are functions of TIRC7 proteins and/or ligands thereof): activation of neutrophils; activation or inhibition of T-cells, B-cells, NK cells, LAK cells, dendritic cells, or other immune system cells; proliferation and/or differentiation of T-cells, B-cells, NK cells, LAK cells, dendritic cells, or other immune system cells; proliferation and/or differentiation of epithelial cells such as breast or intestinal/colonic epithelium cells or keratinocytes. In addition these antibodies preferably capable of altering homotypic and/or heterotypic adhesion among TIRC7 proteins (i.e., TIRC7 family members) or adhesion of TIRC7 proteins to other TIRC7 ligands.

The antibody of the invention can be a monoclonal antibody, a single chain antibody, chimeric antibody, humanized antibody, xenogeneic antibody, fully human antibody, or a fragment and/or a chemically modified derivative of any one thereof that specifically binds TIRC7 antigen also including bispecific antibody, synthetic antibody, antibody fragment, such as Fab, Fv or scFv fragments etc., or a chemically modified derivative of any of these. Antibodies or fragments thereof can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in WO89/09622. Methods for the production of humanized antibodies are described in, e.g., EP-A1 0 239 400 and WO90/07861. A further source of antibodies to be utilized in accordance with the present invention are so-called xenogeneic antibodies. The general principle for the production of xenogeneic antibodies such as human antibodies in mice is described in, e.g., WO 91/10741, WO 94/02602, WO 96/34096 and WO 96/33735. As discussed above, the antibody of the invention may exist in a variety of forms besides complete antibodies; including, for example, Fv, Fab and F(ab)2, as well as in single chains; see e.g. WO88/09344. In case of bispecific antibodies where one specificity is directed to TIRC7 and the other preferably to a T cell antigen such as CD3, it is advantageous if the binding site recognizing TIRC7 has a high affinity in order to capture the antigen target cells. On the other hand, the binding affinity of the binding site recognizing, e.g., a T cell stimulatory molecule should be in the order of those of the natural T cell receptor/ligand interaction or of that usually found for the interaction of the T-cell costimulatory molecules with their receptor.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y.

Modifications of the antibody of the invention include chemical and/or enzymatic derivatizations at one or more constituent amino acid, including side chain modifications, backbone modifications, and N— and C-terminal modifications including acetylation, hydroxylation, methylation, amidation, and the attachment of carbohydrate or lipid moieties, cofactors, and the like. Likewise, the present invention encompasses chimeric proteins which comprise the described anti-TIRC7 antibody or some fragment thereof at the amino terminus fused to heterologous molecule such as an immunostimulatory ligand at the carboxyl terminus; see, e.g., WO00/30680 for corresponding technical details.

Hence, the present invention relates to any antibody and similar binding molecules which recognize the same epitope and with substantially the same affinity, or at least ⅟10 of the affinity as the antibodies of the invention exemplified herein. Such antibodies and binding molecules can be tested for their binding specificity and affinity by for example by using peptide 6 (a peptide having the amino acid sequence of SEQ ID NO: 6) and/or competitive assays with the an antibody described in the examples.

In a preferred embodiment, the antibody of the invention is a chimeric or a humanized antibody. Chimeric antibodies are antibodies whose light and heavy chain genes have been constructed, typically by genetic engineering, from immunoglobulin gene segments belonging to different species. For example, the variable (V) segments of the genes from the mouse TIRC7 monoclonal antibody may be joined to human constant (C) segments, such as γ1 and γ3. A typical therapeutic chimeric antibody is thus a hybrid protein consisting of the V or antigen-binding domain from a mouse antibody and the C or effector domain from a human antibody, although other mammalian species may be used as well if for example veterinary application is envisaged. Human constant region DNA sequences can be isolated in accordance with well known procedures from a variety of human cells, but preferably immortalized B-cells (see, Kabat op. cit. and WO87/02671). For example, the human kappa immunoglobulin constant and J region genes and sequences are described in Heiter, Cell 22 (1980), 197-207 and the nucleotide sequence of a human immunoglobulin C gene is described in Ellison, Nucl. Acids Res. 10 (1982), 4071, both of which are incorporated herein by reference. In a particularly preferred embodiment, the antibody of the invention comprises the amino acid sequence of the $V_H$ and/or $V_L$ region as depicted in FIGS. 1 and 2, and FIGS. 9 and 10, respectively.

In a further embodiment, the present invention relates to an antigen or an epitope thereof which is recognized by an antibody of the invention. Said antigen or epitope may be glycosylated, unglycosylated or partially deglycosylated. As discussed herein and explained in the examples, the present invention features antigens which are particularly suited for eliciting an immune response. For the identification and isolation of antigen and epitopes of the invention conventional epitope mapping can be used; see, e.g., Harlow and Lane, supra. Furthermore, e.g., cDNA libraries can be screened by injecting various cDNAs into oocytes, allowing sufficient time for expression of the cDNA gene products to occur, and testing for the presence of the desired cDNA expression product, for example, by using the antibody of the invention. Alternatively, a cDNA expression library in E. coli can be screened indirectly for peptides having at least one epitope of the invention using antibodies of the invention (Chang and Gottlieb, J. Neurosci., 8:2123, 1988). After having revealed the structure of such antigens the rational design of binding partners and/or domains may be possible. For example, folding simulations and computer redesign of structural motifs can be performed using appropriate computer programs (Olszewski, Proteins 25 (1996), 286-299; Hoffman, Comput. Appl. Biosci. 11 (1995), 675-679). Furthermore, computers can be used for the conformational and energetic analysis of detailed protein models (Monge, J. Mol. Biol. 247 (1995), 995-1012; Renouf, Adv. Exp. Med. Biol. 376 (1995), 37-45). Preferably, the antigen of the invention does not comprise more that 50, preferably not more than 40, and still more preferably not more 30 consecutive amino acids from TIRC7 protein. Preferably, the antigens of the present invention have about 12 to 30 amino acids derived from TIRC7. In a most preferred embodiment, said antigen comprises or consists of the amino acid sequence of peptide 7c (SEQ ID No: 5) or 6 (SEQ ID No: 6); see supra. This includes peptides that have been modified or derivatized, such as by glycosylation, acetylation, phosphorylation, and the like.

In another embodiment the present invention relates to a polynucleotide encoding at least a variable region of an immunoglobulin chain of any of the before described antibodies of the invention. One form of immunoglobulin constitutes the basic structural unit of an antibody. This form is a tetramer and consists of two identical pairs of immunoglobulin chains, each pair having one light and one heavy chain. In each pair, the light and heavy chain variable regions or domains are together responsible for binding to an antigen, and the constant regions are responsible for the antibody effector functions. In addition to antibodies, immunoglobulins may exist in a variety of other forms (including less than full-length that retain the desired activities), including, for example, Fv, Fab, and F(ab')$_2$, as well as single chain antibodies (e.g., Huston, Proc. Nat Acad. Sci. USA 85 (1988), 5879-5883 and Bird, Science 242 (1988), 423426); see also supra. An immunoglobulin light or heavy chain variable domain consists of a "framework" region interrupted by three hypervariable regions, also called CDR's; see supra. The antibodies of the present invention can be produced by expressing recombinant DNA segments encoding the heavy and light immunoglobulin chain(s) of the antibody invention either alone or in combination.

The polynucleotide of the invention encoding the above described antibody may be, e.g., DNA, cDNA, RNA or synthetically produced DNA or RNA or a recombinantly produced chimeric nucleic acid molecule comprising any of those polynucleotides either alone or in combination. Preferably said polynucleotide is part of a vector. Such vectors may comprise further genes such as marker genes which allow for the selection of said vector in a suitable host cell and under suitable conditions. Preferably, the polynucleotide of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. In this respect, the person skilled in the art will readily appreciate that the polynucleotides encoding at least the variable domain of the light and/or heavy chain may encode the variable domains of both immunoglobulin chains or only one. Likewise, said polynucleotides may be under the control of the same promoter or may be separately controlled for expression. Possible regulatory elements permitting expression in prokaryotic host cells comprise, e.g., the PL, lac, trp or tac promoter in E. coli, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an C— or N-terminal identification peptide imparting desired characteristics, e.g., stabilization or simplified purification of expressed recombinant product In this context, suitable expression vectors are known in the art such as Okayama-Berg cDNA expression vector pcDV1 (Pharmacia), pCDM8, pRc/CMV, pcDNA1, pcDNA3 (Invitrogene), or pSPORT1 (GIBCO BRL).

Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the immunoglobulin light chains, heavy chains, light/heavy chain dimers or intact antibodies, binding fragments or other immunoglobulin forms may follow; see, Beychok, Cells of Immunoglobulin Synthesis, Academic Press, N.Y., (1979); see also, e.g., the appended examples.

As described above, the polynucleotide of the invention can be used alone or as part of a vector to express the (poly) peptide of the invention in cells, for, e.g., gene therapy or diagnostics of diseases related to immune diseases. The polynucleotides or vectors of the invention are introduced into the cells which in turn produce the antibody. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Isner, Lancet 348 (1996), 370-374; Muhlhauser, Circ. Res. 77 (1995), 1077-1086; Wang, Nature Medicine 2 (1996), 714-716; WO94/29469; WO 97/00957 or Schaper, Current Opinion in Biotechnology 7 (1996), 635-640, and references cited therein. The polynucleotides and vectors of the invention may be designed for direct introduction or for introduction via liposomes, or viral vectors (e.g. adenoviral, retroviral) into the cell. Preferably, said cell is a germ line cell, embryonic cell, or egg cell or derived therefrom, most preferably said cell is a stem cell.

Furthermore, the present invention relates to vectors, particularly plasmids, cosmids, viruses and bacteriophages used conventionally in genetic engineering that comprise a polynucleotide encoding a variable domain of an immunoglobulin chain of an antibody of the invention; optionally in combination with a polynucleotide of the invention that encodes the variable domain of the other immunoglobulin chain of the antibody of the invention. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the polynucleotides and vectors of the invention can be reconstituted into liposomes for delivery to target cells. The vectors containing the polynucleotides of the invention (e.g., the heavy and/or light variable domain(s) of the immunoglobulin chains encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra.

The present invention furthermore relates to host cells transformed with a polynucleotide or vector of the invention. Said host cell may be a prokaryotic or eukaryotic cell. The polynucleotide or vector of the invention which is present in the host cell may either be integrated into the genome of the host cell or it may be maintained extrachromosomally. The host cell can be any prokaryotic or eukaryotic cell, such as a bacterial, insect, fungal, plant, animal or human cell. Preferred fungal cells are, for example, those of the genus *Saccharomyces*, in particular those of the species *S. cerevisiae*. The term "prokaryotic" is meant to include all bacteria which can be transformed or transfected with a DNA or RNA molecules for the expression of an antibody of the invention or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells, most preferably NSO and CHO cells. Depending upon the host employed in a recombinant production procedure, the antibodies or immunoglobulin chains encoded by the polynucleotide of the present invention may be glycosylated or may be non-glycosylated. Antibodies of the invention or the corresponding immunoglobulin chains may also include an initial methionine amino acid residue. A polynucleotide of the invention can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, Molecular Cloning: A Laboratory Manual, Cold Spring Harbor Laboratory, Cold Spring Harbor, N.Y., 1989). The genetic constructs and methods described therein can be utilized for expression of the antibody of the invention or the corresponding immunoglobulin chains in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Suitable source cells for the DNA sequences and host cells for immunoglobulin expression and secretion can be obtained from a number of sources, such as the American Type Culture Collection ("Catalogue of Cell Lines and Hybridomas," Fifth edition (1985) Rockville, Md., U.S.A., which is incorporated herein by reference). Furthermore, transgenic animals, preferably mammals, comprising cells of the invention may be used for the large scale production of the antibody of the invention.

Thus, in a further embodiment, the present invention relates to a method for the production of an antibody of the invention or a binding fragment or immunglobulin chain(s) thereof comprising (a) culturing the cell of the invention; and
(b) isolating said antibody or binding fragment or immunoglobulin chain(s) thereof from the culture, The transformed hosts can be grown in fermentors and cultured according to techniques known in the art to achieve optimal cell growth. Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like; see, Scopes, "Protein Purification", Springer-Verlag, N.Y. (1982). The antibody or its corresponding immunoglobulin chain(s) of the invention can then be isolated from the growth medium, cellular lysates, or cellular membrane fractions. The isolation and purification of the, e.g., microbially expressed antibodies or immunoglobulin chains of the invention may be by any conventional means such as, for example, preparative chromatographic separations and immunological separations such as those involving the use of monoclonal or polyclonal antibodies directed, e.g., against the constant region of the antibody of the invention. It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level. The DNAs are then expressed in a suitable host system, and the expressed proteins are collected and renatured, if necessary.

Substantially pure immunoglobulins of at least about 90 to 95% homogeneity are preferred, and 98 to 99% or more homogeneity most preferred, for pharmaceutical uses. Once purified, partially or to homogeneity as desired, the antibodies may then be used therapeutically (including extracorporeally) or in developing and performing assay procedures.

The present invention also involves a method for producing cells capable of expressing an antibody of the invention or its corresponding immunoglobulin chain(s) comprising genetically engineering cells with the polynucleotide or with the vector of the invention. The cells obtainable by the method of the invention can be used, for example, to test the interaction of the antibody of the invention with its antigen.

Furthermore, the invention relates to an antibody, an immunoglobulin chain thereof and to a binding fragment thereof encoded by a polynucleotide according to the invention or obtainable by the above-described methods or from cells produced by the method described above. The antibody of the invention can be characterized in that it competes with an antibody comprising the variable regions shown in FIGS. 1 and 2, and FIGS. 9 and 10, respectively, for binding a peptide comprising amino acid sequence DLPDASVNG-WSSDE (peptide 6, SEQ ID NO: 6). The antibodies of the present invention will typically find use individually in treating substantially any disease susceptible to monoclonal antibody-based therapy. In particular, the immunoglobulins can be used as immunosuppressive agents. For an antibody of the invention, typical disease states suitable for treatment include inflammatory symptoms.

The antibodies can be used therapeutically in, e.g., patients suffering from a disease related the to immune response; see supra. Such therapy can be accomplished by, for example, the administration of antibodies, antigens or epitopes of the invention. Such administration can utilize unlabeled as well as labeled antibodies or antigens. Labeling agents can be coupled either directly or indirectly to the antibodies or antigens of the invention. One example of indirect coupling is by use of a spacer moiety. Furthermore, the antibodies of the present invention can comprise a further domain, said domain being linked by covalent or non-covalent bonds. The linkage can be based on genetic fusion according to the methods known in the art and described above or can be performed by, e.g., chemical cross-linking as described in, e.g., WO94/04686. The additional domain present in the fusion protein comprising the antibody of the invention may preferably be linked by a flexible linker, advantageously a polypeptide linker, wherein said polypeptide linker comprises plural, hydrophilic, peptide-bonded amino acids of a length sufficient to span the distance between the C-terminal end of said further domain and the N-terminal end of the antibody of the invention or vice versa. The above described fusion protein may further comprise a cleavable linker or cleavage site for proteinases. These spacer moieties, in turn, can be either insoluble or soluble (Diener et al., Science 231 (1986),148) and can be selected to enable drug release from the antigen at the target site. Examples of therapeutic agents which can be coupled to the antibodies, antigens and epitopes of the invention for immunotherapy are drugs, radioisotopes, lectins, and toxins. The drugs with which can be conjugated to the antibodies, antigens and epitopes of the invention include compounds which are classically referred to as drugs such as mitomycin C, daunorubicin, and vinblastine. In using radioisotopically conjugated antibodies, antigens or epitopes of the invention for, e.g., immunotherapy, certain isotopes may be more preferable than others depending on such factors as leukocyte distribution as well as stability and emission. Depending on the autoimmune response, some emitters may be preferable to others. In general, α and β particle-emitting radioisotopes are preferred in immunotherapy. Preferred are short range, high energy a emitters such as $^{212}$Bi. Examples of radioisotopes which can be bound to the antibodies, antigens or epitopes of the invention for therapeutic purposes are $^{125}$I, $^{131}$I, $^{90}$Y, $^{67}$Cu, $^{212}$Bi, $^{212}$At, $^{211}$Pb, $^{47}$Sc, $^{109}$Pd and $^{188}$Re. Other therapeutic agents which can be coupled to the antibody, antigen or epitope of the invention, as well as ex vivo and in vivo therapeutic protocols, are known, or can be easily ascertained, by those of ordinary skill in the art. Wherever appropriate the person skilled in the art may use a polynucleotide of the invention encoding any one of the above described antibodies, antigens or the corresponding vectors instead of the proteinaeous material itself.

Moreover, the present invention relates to compositions comprising the aforementioned antibody, antigen or epitope of the invention or chemical derivatives thereof, or the polynucleotide, vector or cell of the invention. The composition of the present invention may further comprise a pharmaceutically acceptable carrier. The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. Aerosol formulations such as nasal spray formulations include purified aqueous or other solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 μg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 μg to 10 mg units per day. If the regimen is a continuous infusion, it should also be in the range of 1 μg to 10 mg units per kilogram of body weight per minute, respectively. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, the pharmaceutical composition of the invention may comprise further agents such as interleukins or interferons depending on the intended use of the pharmaceutical composition.

In a preferred embodiment, the pharmaceutical composition of the present invention comprises at least one second agent, preferably an agent which inhibits T-cell stimulation depending on the intended use. Such agents include, for example, molecules that are capable of blocking or mimicking receptor/ligand interaction or the like which leads to T-cell suppression. Such agents comprise those blocking the activity of, e.g., costimulatory molecules, such as anti-TIRC7 antibodies, anti-TNF-α antibodies, integrins, Ig-superfamily molecules, selectins as well as drugs blocking chemokines and their respective receptor interactions, drugs blocking IL2/IL2-receptor interaction and other conventional immunosuppressive drugs such as IL-2R mAbs, IL-Toxins and IL-Muteins. Examples for costimulatory molecules and their ligands are described in the prior art, e.g., in Schwartz, Cell 71 (1992), 1065-1068. The interruption of the receptor/ligand interactions by using mAbs or soluble CTLA4Ig for the interaction between CD28 to the B7-2 and CTLA4 to B7-1 and B7-2 are described in Blazar, J. Immunol. 157 (1996), 3250-3259; Bluestone, Immunity 2 (1995), 555-559; Linsley, Science 257 (1992), 792-95. Examples for blocking the receptor/ligand interaction by using mAbs to CD40 or CD40L are reported by Burden, Nature 381 (1996), 434-435; Kirk, Proc. Natl. Acad. Sci. USA 94 (1997), 8789-8794. CD2 antigen and its ligand LFA-3 are described in Bagogui Li et al., review in Adhesion Molecules, Fusion proteins, Novel Peptides, and Monoclonal Antibodies, Recent Developments in Transplantation Medicine, Vol. II, 1995, Physicians&Scientists Publishing Co., Inc. and blocking of their interaction by using of mAbs (anti-Leu-5b, OKT11, T11) is reported in Bromberg, Transplantation 51 (1991) 219-225 or CD2.1gG1 fusion protein. The use of monoclonal Abs agains CD4 molecule is described in Cosimi, Surgery 108 (1990), 406-414. CD47 blockade by mAbs is described by Rheinhold, J. Exp. Med. 185 (1997), 1-11. Integins and 1g-superfamily molecules include LFA-1 with its ligand ICAM-1, -2, -3, Mac-1 with its ligand ICAM-1, -3; ICAM-1 with its ligand LFA-1, Mac-1, CD43; ICAM-2 with its ligand LFA-1; ICAM-3 with its ligand LFA-1, Mac-1; $V_L A4$ and VCAM-1 see, e.g., David, Adams, review in Adhesion Molecules, Fusion proteins, Novel Peptides, and Monoclonal Antibodies, Recent Developments in Transplantation Medicine, Vol. II, 1995, Physicians&Scientists Publishing Co., Inc.; Isobe, Science, 255 (1992), 1125-1127; Cosimi, J. Immunology 144 (1990), 4604-4612; Hynes, Cell 69 (1992),11-25.

Furthermore selectively interfering agents with $V_L A$-4 mAbs to the alpha4 integrin chain (CD49d) can be used, beta1 integrin chain (CD29), or an activation-induced neo-epitope of $V_L A$-4 as well as soluble $V_L A$-4 ligands such as soluble fibronectin or its relevant peptide (GPEILDVPST, SEQ ID NO: 7), or soluble VCAM-1 or its relevant peptide. More selectively blocking agents are antisense oligonucleotides, designed to selectively hybridize with cytoplasmic alpha4, beta1, or VCAM-1 mRNA; Fedoseyeva, J. Immunol. 57 (1994), 606-612.

Another example is the drug pentoxifylline (PTX) that is able to block expression of VCAM-1; Besler, J. Leukoc. Biol. 40 (1986), 747-754. Furthermore, VCAM-1 mAb, M/K-2, anti-murine, for example could prolong allograft survival, Orosz, Transplantation, 56 (1993), 453-460. Blocking of members of the integrin family and their ligands by using mAbs is decribed in Kupiec-Weglinski, review in Adhesion Molecules, Fusion proteins, Novel Peptides, and Monoclonal Antibodies, Recent Developments in Transplantation Medicine, Vol. II, 1995, Physicians&Scientists Publishing Co., Inc. Selectins, e.g., L-selectin (CD62L), E-selectin (CD62E), P-selectin (CD62P) have been described in Forrest and Paulson, Selectin family of adhesion molecules. In: Granger and Schmid-Schonbein, eds. Physiology and Pathophysiology of Leukocyte Adhesion. New York, Oxford Press, 1995, pp 68-146. The combination of conventional immunosuppressive drugs, e.g., ATG, ALG, OKT3, Azathioprine, Mycophenylate, Mofetyl, Cyclosporin A, FK506, Sirolimus (Rapamune), Corticosteroids may be used as decribed in Cosimi, Transplantation 32 (1981), 535-539; Shield, Transplantation 38 (1984), 695-701, and Graft, June 2001, Vol 4 (4). The interruption of chemokines and interactions with their respective receptor by using mAbs is reviewed in Luster, Chemokines-chemotactic cytokines that mediate inflammation, New Engl. J. Med. February (1998), 436-445. Thus, any agent as defined above and referenced by way of example can be used in accordance with the pharmaceutical composition of the invention or the methods and uses described herein.

Furthermore, the pharmaceutical composition may also be formulated as a vaccine, for example, if the pharmaceutical composition of the invention comprises an antigen as described above that is capable of eliciting an effective immune response against TIRC7. Advantageously, the pharmaceutical composition of the invention is intended for use in organ transplantation or in the treatment of an inflammatory disease.

Therapeutic or diagnostic compositions of the invention are administered to an individual in a therapeutically effective dose sufficient to treat or diagnose disorders in which modulation of TIRC7-related activity is indicated. The effective amount may vary according to a variety of factors such as the individual's condition, weight, sex and age. Other factors include the mode of administration. The pharmaceutical compositions may be provided to the individual by a variety of routes such as by intracoronary, intraperitoneal, subcutaneous, intravenous, transdermal, intrasynovial, intramuscular or oral routes. In addition, co-administration or sequential administration of other agents may be desirable.

A therapeutically effective dose refers to that amount of antibodies, antigens, polynucleotides and vectors of the invention ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

Thus, the present invention relates to the use of the antibody and the antigen of the invention for the preparation of a pharmaceutical composition for inhibition of an immune response, preferably for the treatment of graft versus host disease, autoimmune diseases, allergic diseases, infectious diseases, sepsis, for the treatment of tumors, for the improvement of wound healing or for inducing or maintaining immune unresponsiveness in a subject; see also supra.

Accordingly, the present invention also relates to a method of modulating the immune response in a subject in need thereof, comprising administering the antibody or the antigen of the invention. Compositions comprising the antibody or the antigen of this invention can be added to cells in culture (in vitro) or used to treat patients, such as mammals (in vivo). Where the antibody or the antigen are used to treat a patient, the polypeptide is preferably combined in a pharmaceutical composition with a pharmaceutically acceptable carrier such as a larger molecule to promote polypeptide stability or a pharmaceutically acceptable buffer that serves as a carrier for the antibodies that has more than one antibody coupled to a single entity. The methods of the invention include administering to a patient, preferably a mammal, and more preferably a human, the composition of the invention in an amount effective to produce the desired effect. The antibody or the antigen can be administered as a single dose or in multiple doses. Useful dosages of the active agents can be determined by comparing their in vitro activity and the in vivo activity in animal models. Methods for extrapolation of effective dosages in mice, and other animals, to humans are known in the art. The present invention also provides a method of modulating (e.g., activating or inhibiting) immune cell (e.g., T-cells, B-cells, NK cells, LAK cells, or dendritic cells) activation, proliferation, and/or differentiation that includes contacting an immune cell with a antibody or the antigen described above.

From the foregoing, it is evident that the present invention encompasses any use of a ligand binding molecule comprising at least one CDR of the above described antibody, in particular for diagnosing and/or treatment of a disorder related to the aberrant expression or malfunction of T-cell immune response cDNA 7 (TIRC7). Preferably, said ligand binding molecule is an antibody of the present invention or an immunoglobulin chain thereof.

The biological activity of the antibodies identified here suggests that they have sufficient affinity to make them potential candidates for drug localization to cells expressing the appropriate surface structures. This targeting and binding to cells could be useful for the delivery of therapeutically active agents (including targeting drugs, DNA sequences, RNA sequences, lipids, proteins (e.g., human growth factors) and gene therapy/gene delivery. More preferably, the therapeutically active agent is an anti-inflammatory agent. Molecules/particles with an anti-TIRC7 antibody would bind specifically to cells/tissues expressing TIRC7, and therefore could have diagnostic and therapeutic use. Thus, the antibody or the antigen of the present invention can be labeled (e.g., fluorescent, radioactive, enzyme, nuclear magnetic) and used to detect specific targets in vivo or in vitro including "immunochemistry" like assays in vitro. In vivo they could be used in a manner similar to nuclear medicine imaging techniques to detect tissues, cells, or other material expressing TIRC7. Another method involves delivering a therapeutically active agent to a patient. The method includes administering at least one antibody or the antigen and the therapeutically active agent to a patient. Preferably, the therapeutically active agent is selected from drugs, DNA sequences, RNA sequences, proteins, lipids, and combinations thereof. More preferably, the therapeutically active agent is an antibacterial agent, anti-inflammatory agent, or antineoplastic agent.

In another embodiment the present invention relates to a diagnostic composition comprising any one of the above described the antibodies, antigens, polynucleotides, vectors or cells of the invention and optionally suitable means for detection. The antigens and antibodies of the invention are, for example, suited for use in immunoassays in which they can be utilized in liquid phase or bound to a solid phase carrier. Examples of immunoassays which can utilize the antigen of the invention are competitive and non-competitive immunoassays in either a direct or indirect format. Examples of such immunoassays are the radioimmunoassay (RIA), the sandwich (immunometric assay) and the Western blot assay. The antigens and antibodies of the invention can be bound to many different carriers and used to isolate cells specifically bound to said polypeptides. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the antibodies of the invention may also be used in a method for the diagnosis of TIRC7 related diseases in an individual by obtaining a body fluid sample from the tested individual which may be a blood sample, a lymph sample or any other body fluid sample and contacting the body fluid sample with an antibody of the invention under conditions enabling the formation of antibody-antigen complexes. The level of such complexes is then determined by methods known in the art, a level significantly higher than that formed in a control sample indicating the disease in the tested individual. In the same manner, the specific antigen bound by the antibodies of the invention may also be used. Thus, the present invention relates to an in vitro immunoassay comprising the antibody or the antigen of the invention.

Furthermore, the present invention relates to an oligonucleotide comprising a nucleotide sequence of any one of SEQ ID NOS: 12 to 40 and their use for the cloning of an anti-TIRC7 antibody; see the appended examples.

In a further aspect, the present invention relates to the use of T-cell immune response cDNA 7 (TIRC7) antagonist and an anti-inflammatory drug for the preparation of pharmaceutical composition for the prevention or treatment of an inflammatory disease. This aspect of the invention is based on the surprising finding that combination therapy, involving the use of TIRC7 antagonist, in the example anti-TIRC7 antibody in conjunction with an anti-inflammatory drug, in the example an TNF-α antagonist, produces markedly superior results than the use of each agent alone in the treatment of an inflammatory disease, particularly in rheumatoid arthritis. Hence, a combination therapy of an inflammatory disease with said pharmaceutical composition promotes a positive therapeutic response in a treated subject, which response is greater than a therapeutic response that would be observed with therapy using said anti-inflammatory drug alone.

In particular, it could be surprisingly shown that an anti-TIRC7 mouse monoclonal antibody herein also called murine Neliximab alone as well as in combination with Enbrel shows significant therapeutic activity in RA mice model in comparison to Enbrel and control antibody treated and non-treated mice with an unexpected synergistic effect when using Neliximab and Enbrel together at half of their concentration compared to the corresponding monotherapy; see Example 10 and FIG. 6. However, besides the improvement of the clinical score in the therapeutic treatment of CIA, it could be surprisingly shown that when the individual animals of each group were analysed, the number of non-responder in the combination therapy was less than could be expected from each individual group; see FIG. 7. Thus, treatment with both Neliximab and Enbrel is efficacious for subjects which do not respond to either of those drugs alone. On the basis of these findings in an in vivo mice model, it is concluded that therapy of inflammatory diseases with TIRC7 antagonist such as anti-TIRC7 antibodies in conjunction with other anti-inflammatory drugs opens up a way for the treatment of arthritis patients which hitherto have not been amenable to therapeutic treatment. Furthermore, the synergistic effect of the combination therapy provides more efficient treatment regimens with less side effects.

The phrase "combination therapy" (or "co-therapy") embraces the administration of a TIRC7 antagonist and another anti-inflammatory drug as part of a specific treatment regimen intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" generally is not intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule or intravenous injection having a fixed ratio of each therapeutic agent or in multiple, single capsules or intravenous injections for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection.

Anti-inflammatory drugs to be combined with the TIRC7 antagonist for use in accordance with the present invention include but are not limited to TNF-A antagonists, methotrexate, cyclosporin, IL-1 inhibitors (Kineret®), blocker of IL-1 receptor, COX inhibitors, T-cell activation inhibitors (CTLA4Ig, LEA29Y), blocker of ICAM-1, LFA-1 or other antibodies against membrane or non-membrane proteins, non-steroidal anti-inflammatory drug (NSAID), or other DMARDs, e.g. oral Gold, Azathioprine, cyclophosphamide, hydroxychloroquine sulfate, leflunomide, minocycline, penicollamine, sulfasalazine, or aurothioglucose gold sodium thiomalate; see also the background section above. The anti-inflammatory drugs preferably include agents interfering with cytokines with anti-inflammatory properties, such as IL-2, IL-4 and IL-10. Since those cytokines, as TNF-α, are left unaffected by the treatment with Neliximab, it may be expected that a combination of TIRC7 antagonist with an antagonist of IL-2, IL-4 or IL-10 at least gives rise to additive therapeutic effect. Thus, the present invention also concerns the treatment of inflammatory diseases, such as rheumatoid arthritis, through the administration of TIRC7 antagonist such as anti-TIRC7 antibody in conjunction with IL-2, IL-4 or IL-10 antagonist.

Preferably, the anti-inflammatory drug is a TNF-α antagonist. The term "TNF-α antagonist" or "TNF antagonist" refers to, for example, soluble tumor necrosis factor receptor and tumor necrosis factor binding proteins that bind to tumor necrosis factor and prevent tumor necrosis factor from binding to cell membrane bound tumor necrosis factor receptors. Such proteins competitively bind to cell surface receptors or intracellular tumor necrosis factor recognition sites displacing tumor necrosis factor or preventing tumor necrosis factor from binding to or interacting with the cells, therefore suppressing the biological activities caused by tumor necrosis factor. Tumor necrosis factor antagonizing agents that can be used in the present invention include, but not limited to those described in WO01/00229 and WO0149321, hereby incorporated by reference.

Thus, in one embodiment said TNF antagonist is selected from the group consisting of etanercept, infliximab, Pegsunercept, pegylated soluble TNF receptor Type I (PEGsTNF-R1), CDP571 (a humanized monoclonal anti-TNF-alpha antibody), and D2E7 (a human anti-TNF mAb).

In a preferred embodiment, the tumor necrosis factor antagonist that may be used in the present invention is etanercept (ENBREL; Immunex Corp), or its biologically active equivalent. ENBREL is described in U.S. Pat. No. 5,605,690 and is hereby incorporated by reference. ENBREL is a recombinant version of the soluble p75 Tumor Necrosis Factor receptor (TNFR) linked to the Fc portion of human IgG1. It inhibits tumor necrosis factor biological activity by acting as a competitive inhibitor to the binding of tumor necrosis factor to its cell receptors. For treatment of arthritis or inflammation, tumor necrosis factor is administered in systemic amounts ranging from about 0.1 mg/kg/week to about 100 mg/kg/week. In one embodiment of the present invention, tumor necrosis factor antagonist is administered in amounts ranging from about 0.5 mg/kg/week to about 50 mg/kg/week. For local intra-articular administration, dosages preferably range from about 0.01 mg/kg to about 1.0 mg/kg per injection. In another embodiment of the present invention the adult dose of ENBREL (etanercept) is 25 mg twice a day, as a subcutaneous injection.

In preferred embodiment, said inflammatory disease to be treated with the composition in accordance with the present invention is arthritis and said TIRC7 antagonist is a TIRC7 antagonist as defined hereinabove. Furthermore, it is preferred that said pharmaceutical composition is in a form adapted for administration to the patient in a dosage and regimen as defined hereinabove or as demonstrated in the examples and shown in FIGS. 3 to 7.

In a particularly preferred aspect, the present invention relates to a pharmaceutical composition comprising a TIRC7 antagonist and a TNF-α antagonist. Preferably, said anti-TIRC7 antagonist is an anti-TIRC7 antibody or fragment thereof and said TNF-α antagonist is a compound as defined hereinbefore. In a particularly preferred embodiment the pharmaceutical composition of the present invention comprises Neliximab or an equivalent antibody and etanercept or infliximab.

Any one of the above-described pharmaceutical compositions for use in accordance with the present invention may comprise further anti-inflammatory drugs, such as those mentioned hereinbefore and in the background section, for example the anti-rheumatic drugs methotrexate or cyclosporin A, which can be administered in conjunction with the TIRC7 antagonist and for example a TNF-α antagonist.

The combination therapy of the current invention is thus useful for the treatment of many autoimmune or inflammatory diseases of humans and of animals. In humans, diseases for which the therapy is appropriate include rheumatoid arthritis (RA) and juvenile chronic arthritis (JCA). Other diseases and conditions for which combination therapy is appropriate include spondyloarthropathies, such as ankylosing spondylitis, psoriatic arthritis, or arthritis associated with inflammatory bowel disease; vasculitis syndromes, such as polyarteritis nodosa, Wegener's granulomatosis, giant cell arthritis, Henoch-Schonlein purpura, and microscopic vasculitis of the kidneys; Sjogren's syndrome; systemic lupus erythematosus; inflammatory bowel disease, including Crohn's disease and ulcerative colitis; chronic active hepatitis; primary biliary cirrhosis; cryptogenic fibrosing alveolitis and other fibrotic lung diseases; uveitis; multiple sclerosis; myasthenia gravis; hemolytic anemia; scleroderma; graft versus host disease; allergy; and transplantation of kidneys, liver, heart, lungs, bone marrow, skin, or of other organs.

In a particularly preferred embodiment, the pharmaceutical composition described above is for use in the treatment of rheumatoid arthritis.

In accordance with above, the present invention relates to the use of TIRC7 antagonist for the preparation of a pharmaceutical composition for the treatment or prevention of an inflammatory disease for patients receiving previously, concomitantly or subsequently a medicament comprising an anti-inflammatory drug.

Likewise, the present invention relates to the use of an anti-inflammatory drug for the preparation of a pharmaceutical composition for the treatment or prevention of an inflammatory disease for patients receiving previously, concomitantly or subsequently a medicament comprising TIRC7 antagonist.

Said TIRC7 antagonist may be any TIRC7 antagonist as described herein, anti-TIRC7 antibodies, however, being preferred. Similarly, said anti-inflammatory drug may be any one of those described above. Furthermore, TNF antagonists are preferred to be used in combination with TIRC7 antagonist. As described herein before, treatment regimens to be used for treating disorders mentioned above are designed in two general ways: acute regimens, designed to achieve rapid blood levels and rapid action, wherein the TIRC7 and TNF blockade is desired for hours to days; and chronic regimens, wherein the TIRC7 and TNF blockade is desired for days, weeks, or months. TNF antagonists which are suitable for these regimens are etanercept (ENBREL) from Immunex Corporation and infliximab (REMICADE) from Centocor, Inc., in particular etanercept is preferred.

In summary, the present invention relates to a method for preventing or treatment of a mammal subject afflicted with an inflammatory disease, comprising the step of administering to a mammal having or suspected to get an inflammatory disease an amount of TIRC7 antagonist in the range of from 0.5 mg/kg/day to 50 mg/kg/day and wherein said administration is at intervals of one to three times a week during a period of at least two weeks for a therapeutic treatment regimen and at daily intervals over a week for a preventive treatment regimen; said therapeutic treatment regimen and preventive treatment regimen may be combined and/or repeated at one or several intervals; see supra. In addition, the present invention relates to a method for preventing or treatment of a mammal subject afflicted with an inflammatory disease, comprising the step of administering to a mammal having or suspected to get or being predetermined to fall ill with an inflammatory disease a therapeutic effective amount of TIRC7 antagonist in combination with an anti-inflammatory drug; see supra. It is contemplated that yet additional therapies may be employed in the methods. The one or more other therapies may include but are not limited to immunoadjuvants, cytokines, and other non-TIRC7-antibody-based therapies. The anti-inflammatory drug and anti-TIRC7 antibody (and one or more other therapies) may be administered concurrently or sequentially. Where there has been in vivo treatment, a treated mammal can be monitored in various ways well known to the skilled practitioner; see for instance the examples.

For the mentioned uses, articles of manufacture, pharmaceutical compositions and methods of treatment, injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono-or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drugs can be prepared by mixing the drugs with a suitable non-irritating excipient such as cocoa butter, synthetic monodi-or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, a contemplated aromatic sulfone hydroximate inhibitor compound can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated aromatic sulfone hydroximate inhibitor compound can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration. The TIRC7 antagonist, optionally in combination with another anti-inflammatory drug, can be administered in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Optionally, administration may be performed through mini-pump infusion using various commercially available devices.

Effective dosages and schedules for administering TIRC7 antagonist, optionally in combination with another anti-inflammatory drug may be determined in accordance with the above described treatment regimen, and making such determinations is within the skill in the art. Interspecies scaling of dosages can be performed in a manner known in the art, e.g., as disclosed in Mordenti et al., Pharmaceut. Res. 8 (1991), 1351. Those skilled in the art will understand that the dosage of TIRC7 antagonist, optionally in combination with another anti-inflammatory drug, that must be administered will vary depending on, for example, the mammal which will receive the pharmaceutical composition, the route of administration, and other drugs or therapies being administered to the mammal.

A combination of the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques.

The above considerations regarding effective formulations and administration procedures are well known in the art and are described in standard textbooks. Drug formulations are discussed in, for example, Hoover, John E., Remington's Pharmaceutical Sciences, Mack Publishing Co., Easton, Pennsylvania; 1975, hereby incorporated by reference. Another discussion of drug formulations can be found in Liberman, H. A. and Lachman, L., Eds., Pharmaceutical Dosage Forms, Marcel Decker, New York, N.Y., 1980, hereby incorporated by reference.

Besides being useful for human treatment, the method, combinations, agents and compositions of the present invention are also useful for treatment of mammals, including, but not limited to, horses, dogs, cats, rats, mice, sheep, pigs, etc.

Accordingly, an advantage of the present invention is that it provides TIRC7 antagonists for a new pharmacological treatment of inflammatory diseases, in particular rheumatoid arthritis, such that the use of these TIRC7 antagonists will result in the amelioration of these conditions. Furthermore, the present invention provides for the treatment of inflammatory diseases a mono- as well as a combination therapy that reduces inflammation to a subject by inhibiting the action of inflammatory processes in the human body for the immediate, short term (acute conditions) and long term (chronic conditions), such that this reduction in inflammation will produce clinical improvement in the subject and will give the subject a better opportunity to heal, slows disease progression, prevents damage, or otherwise improves the patient's health.

A further advantage of the present invention is that it provides for a treatment of inflammatory diseases for subject which have not been amenable to conventional treatment.

A further advantage of the present invention is that it provides for a particular advantageous TIRC7 antagonist, i.e. an anti-TIRC7 antibody called Neliximab, which is particular useful for the treatment of inflammatory diseases.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

These and other embodiments are disclosed and encompassed by the description and Examples of the present invention. Further literature concerning any one of the antibodies, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. A more complete understanding can be obtained by reference to the following examples which are provided herein for purposes of illustration and are not intended to limit the scope of the invention.

The Figures show:

FIG. 1: $V_H$ sequence (SEQ ID NO:2) of clone 17-1 (SEQ ID NO: 1) (Neliximab)(CDRs are underlined).

FIG. 2: $V_L$ sequence (SEQ ID NO:4) of clone 17-1 (SEQ ID NO: 3) (Neliximab)(CDRs are underlined).

FIG. 3: Neliximab shows significant therapeutic effect in RA model in mice when treatment starts at day 24 after second challenge of the mice with collagen.

Figure 4:
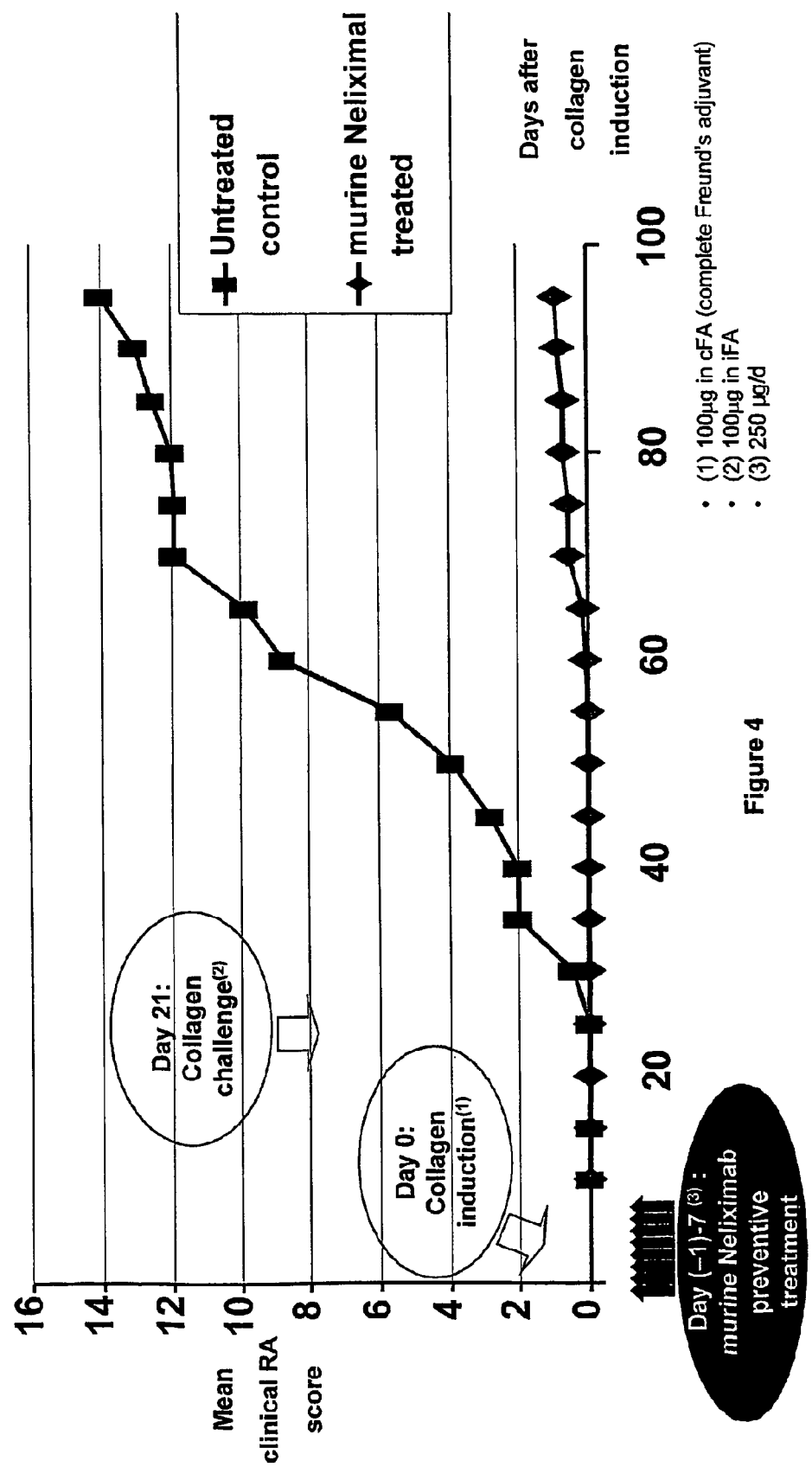

FIG. 4: Preventive activity of murine Neliximab in CIA.

Figure 5:
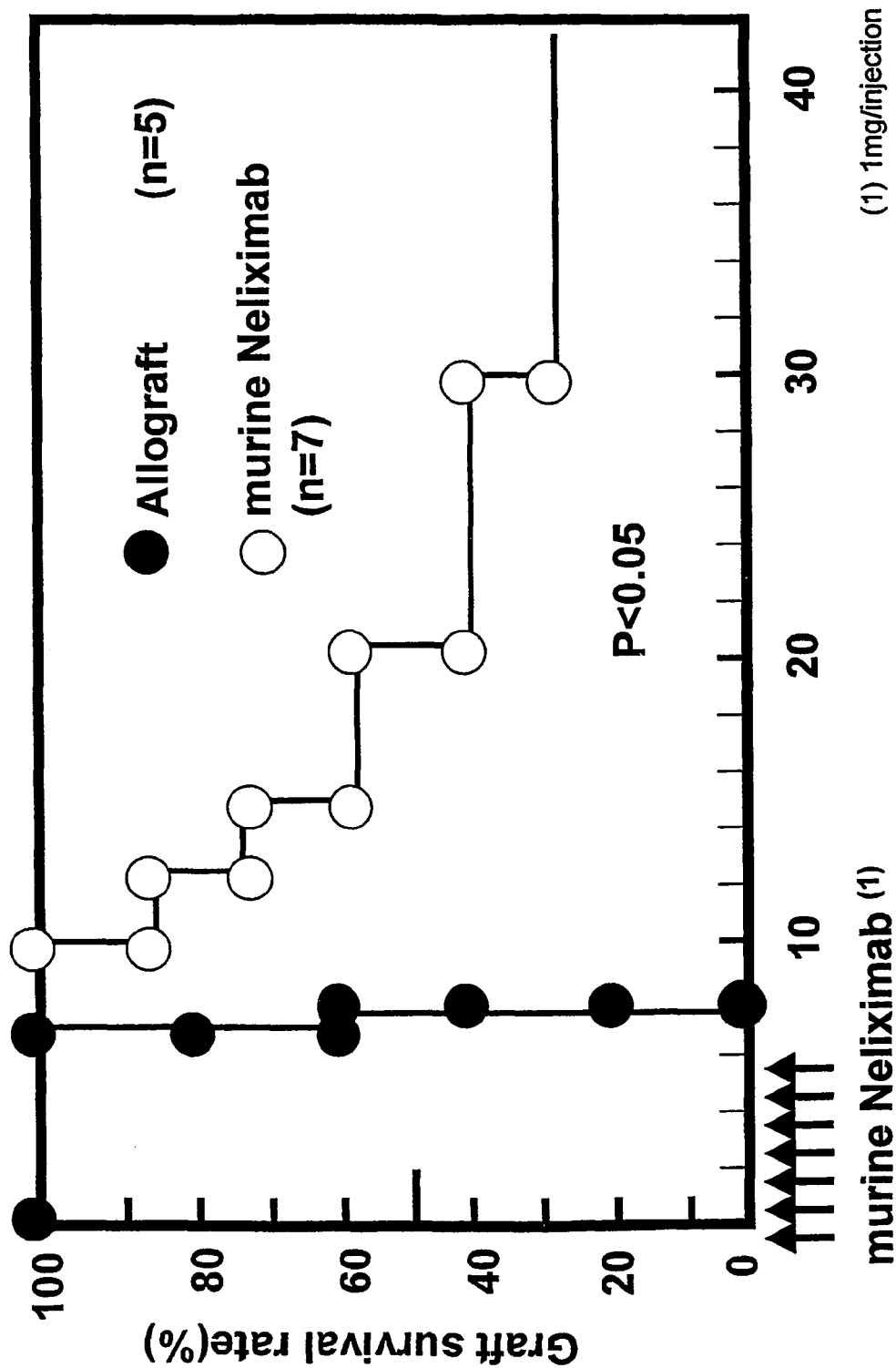

FIG. 5: Effect of murine Neliximab on cardiac allograft survival in mice.

FIG. 6: Neliximab alone or in combination with Enbrel shows with significant therapeutic activity in RA mice model in comparison to Enbrel and control antibody treated and nontreated mice. The combination group received only 250 µg of Neliximab and 25 µg of Enbrel whereas the Neliximab group alone was treated with 500 µg and Enbrel alone was treated with 50 µg pro day. DBA/1 mice were used and disease was induced by collagen (Sigma, 100 µg in cFA and 100 µg in iFA at day 21). Treatment started after animals showed clinical symptome and score of rheumatoid arthritis (Treatment: start of treatment after score 1; mAbs: 500 µg, Enbrel: 50 µg; Neliximab+Enbrel: 250 µg Neliximab+25 µg Enbrel).

Figure 7:
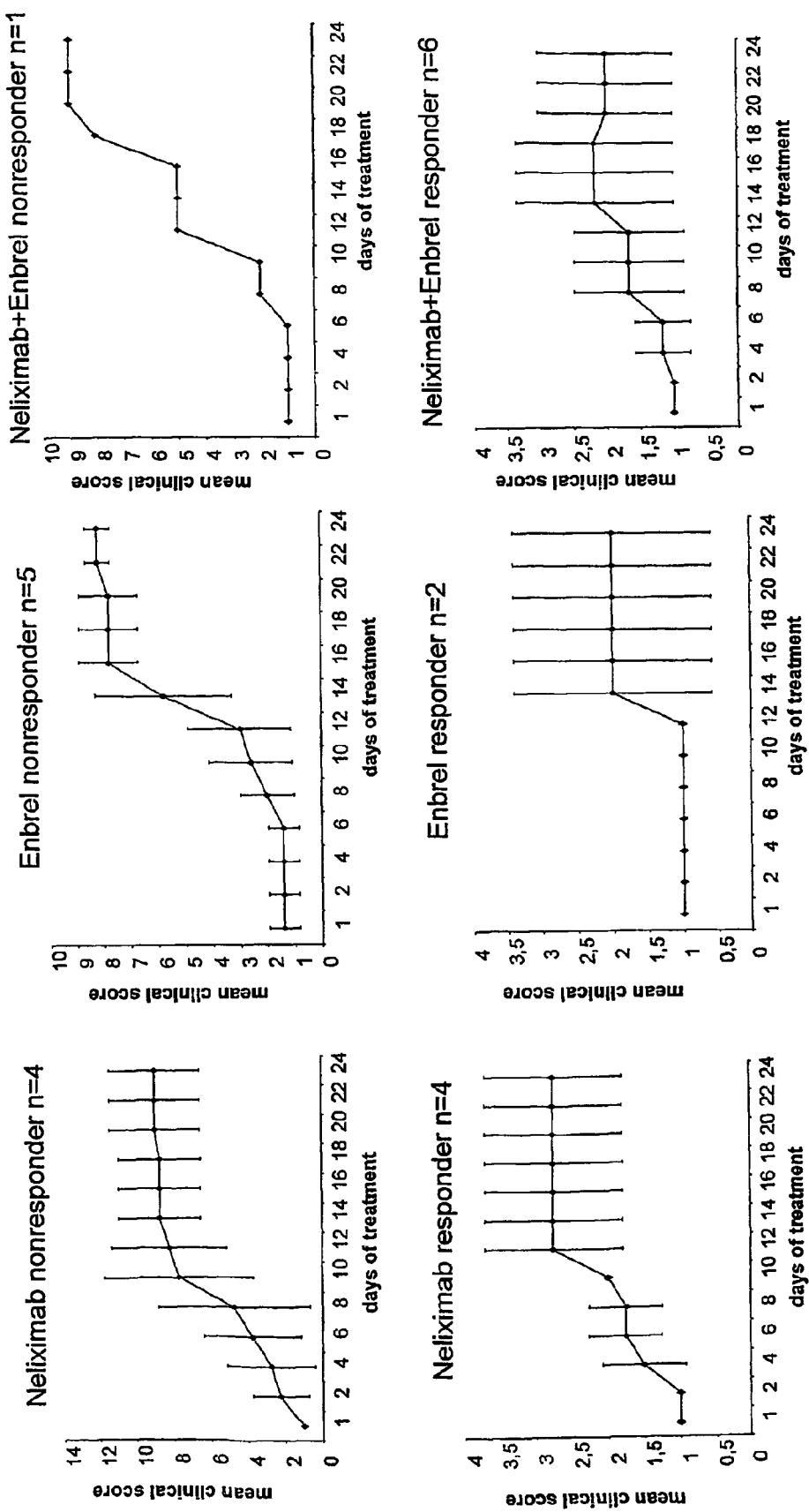

FIG. 7: Therapeutic activity of Neliximab, Enbrel and combination after clinical score of 1 (day 24).

Figure 8:
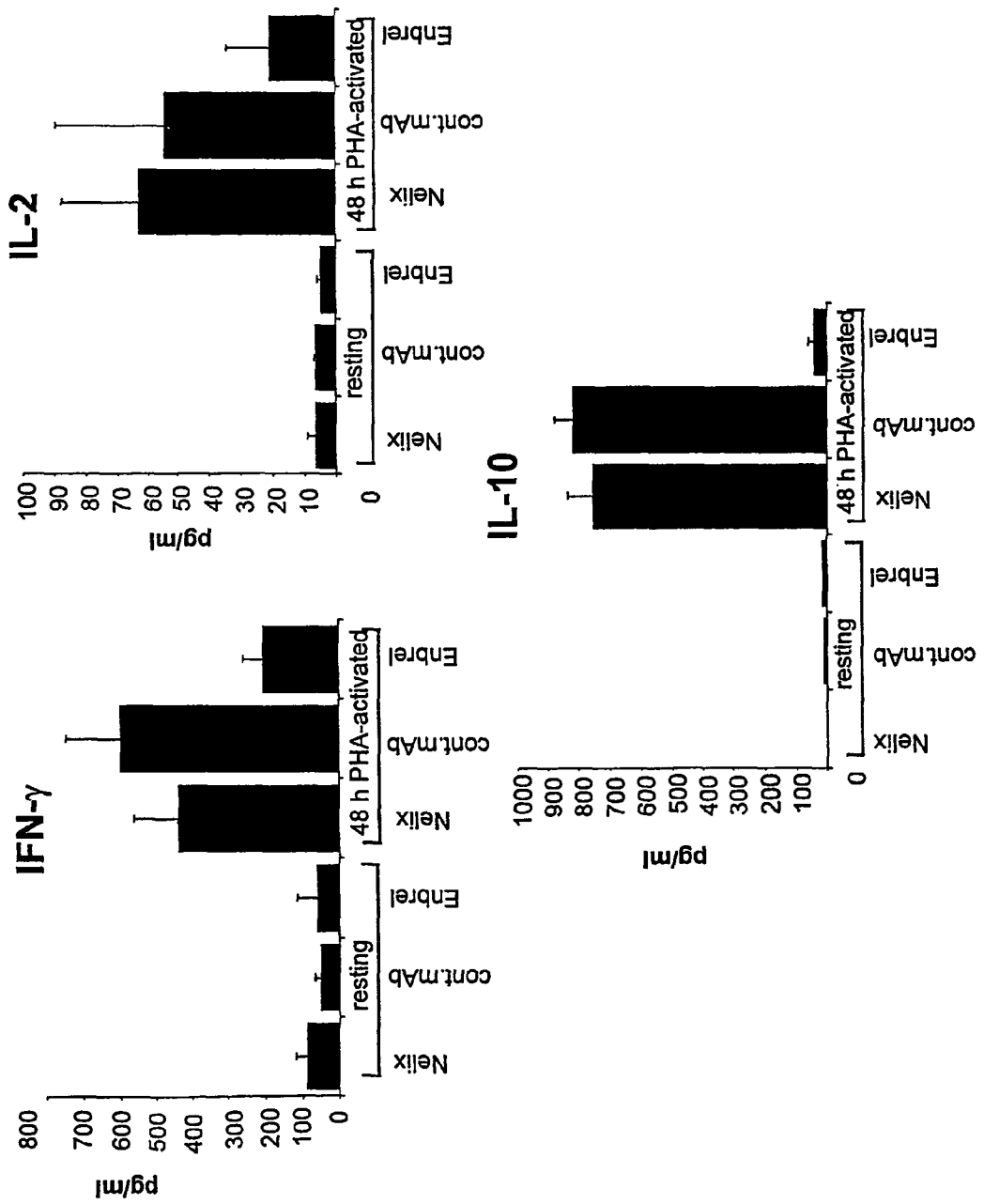

FIG. 8: Neliximab down regulates IFN-γ expression after ex vivo PHA stimulation of splenocytes whereas no changes were observed in IL-2 and IL-10 expression.

FIG. 9: $V_H$ sequence (SEQ ID NO:9) of an allelic variant of clone 17-1 (SEQ ID NO:8) (Neliximab)(CDRs are underlined).

FIG. 10: $V_L$ sequence (SEQ ID NO: 11) of an allelic variant of clone 17-1 (SEQ ID NO:10) (Neliximab).

EXAMPLES

Example 1

Generation and Selection of Monoclonal Antibodies Directed against TIRC7

Balb/c-mice were immunized in presence of Freunds adjuvans with one of six peptides derived from the sequence of several hypothetically extracellular domains of TIRC7. Priming of mice with antigen was followed by several booster injections over a period of 3 months. Fusion of spleen cells with SP2/0-Ag14 myeloma cells was carried out according to the PEG-fusion technique. All together 15 fusions were performed and pursued successfully. After 3 weeks of selection in HAT-media, repeated separation of the cells according to the limiting-dilution method and screening of the supernatants using the ELISA technique 192 stable antibody producing hybribodomas were received. Determination of the antibody isotype revealed that 140 of 192 monoclonal antibodies were IgM antibodies whereas 52 were IgG antibodies. All 52 IgG antibody producing hybridomas were thawed, separated once more and tested regarding their IgG-production. Hybridomas which produced less than 5 µg IgG per ml supernatant after cell death were excluded.

42 antibodies were produced in small volumes of 150-200 ml supernatant and purified using protein A or protein G on a HPLC affinity chromatographic column. Purified antibodies were tested regarding their capacity to inhibit immune response to mitogens as well as their effects on cytokine expression in the supernatants of 48 h activated human cells.

Radioactive Proliferation Assay—Incorporation of $^3$H-thyidine:

PBMC of healthy donors were isolated according to the Ficoll-Paque density centrifugation protocol. Samples of 50000 PBMCs/well were stimulated with PHA (1 µg/ml) and incubated for 48 h at 5% $CO_2$, 37° C. in presence of TIRC7-antibodies and IgG-control antibodies in a total volume of 100 µl/well. Samples were run in triplicates on 96 well-microtiter-plates (MTPs). After 48 h 0.5 µCi $^3$H-thymidine per well were added and the cells were reincubated for additional 18 h. Cells were harvested and lysed using a cell harvester and collected on nitrocellulose-filter-MTPs. Plates were dried at room temperature for 4 h. To enhance the radioactive signal produced by the samples a scintillation fluid was added and counts per minute (cpm) were measured with a beta counter.

Quantitation of Secreted Cytokines in PBMC-Supernatants:

PBMC of healthy donors were isolated according to the Ficoll-Paque density centrifugation protocol. Samples of 50000 PBMCs/well were stimulated with PHA (1 µg/ml) and incubated for 48 h at 5% $CO_2$, 37° C. in presence of TIRC7-antibodies and IgG-control antibodies in a total volume of 100 µl/well. Samples were run in triplicates on 96 well-microtiter-plates (MTPs). After 48 h MTPs were centrifuged at 300×g for 10 min and supernatants collected from the wells. The quantitation of cytokines in the supernatant was carried out on anti-cytokine-antibody-coated microtiter strips provided with the Cytoscreen® ELISA Kit, Biosource. The formerly collected supernatants and diluted standards were incubated in presence of a biotinylated secondary antibody recognizing the specific cytokine for 1.5-3 h at room temperature on these strips depending on the detemined cytokine. Afterwards excessive secondary antibody was removed by washing 3 times with washing buffer. A streptavidin-peroxidase conjugate was added and incubated for 45 min –1 h at room temperature. Excessive conjugate was removed by washing. TMB-substrate-solution was added and the strips incubated for additional 30 min in the dark followed by the addition of stop solution. The colour development was measured at 450 nm and the numbers were statistically analyzed.

The first functional screen led to 15 antibodies which inhibited the proliferation as well as the secretion of IFNγ and IL-2 of PHA-stimulated human PBMC of healthy donors below 30% calculated in relation to the positive control (100%).

The next selection process was performed based on production stability of the hybridoma, stability of the antibody, immunoprecipitating qualities and immunofluorescence staining. Finally one antibody was selected, clone #17, also herein-after called Neliximab, descended from fusions performed with spleen cells of mice that had been immunized with peptides derived from the largest extracellular loop of TIRC7, having isotype IgG1, κ.

Example 2

Development of Chimeric Antibody (Neliximab)

1. Identification of the $V_H$ and $V_L$ Regions of the Antibody Clone 17
    1.1. RNA isolation. As a RNA source hybridoma cells were used expressing the antibody described in Example 1, supra Isolation was done with the RNA isolation colums of QIAGEN (Mini) according to the manufactors instructions.
    1.2. cDNA synthesis. cDNA-synthesis was done with total RNA: 3 µg total RNA in 17 µl volume was incubated with 2 µl cDNA-Primer mentioned in below and incubated for 10 min at 75° C.

Primer sequences for cDNA-synthesis and amplification of murine variable regions ($V_H$ and $V_L$):

A: primer for cDNA-synthesis:

```
of the V_H regions
MOCG12Forcor: CAC AAT TTT CTT GTC CAC CTT GGT CG
              (SEQ ID NO: 41)

of the V_L regions
MOCKFOR:      CTC ATT CCT GTT GAA GCT CTT GAC AAT
              (SEQ ID NO: 42)
```

B: primer for amplification of murine variable regions

```
VH chain:
Back primer
MHV.B1.NcoI   GAA TAG GCC ATG GCG GAT GTG AAG CTG CAG GAG TC
              (SEQ ID NO: 40)
MHV.B2.NcoI   GAA TAG GCC ATG GCG CAG GTG CAG CTG AAG GAG TC
              (SEQ ID NO: 13)
MHV.B3.NcoI   GAA TAG GCC ATG GCG CAG GTG CAG CTG AAG CAG TC
              (SEQ ID NO: 14)
```

```
MHV.B4.NcoI   GAA TAG GCC ATG GCG CAG GTT ACT CTG AAA GAG TC
              (SEQ ID NO: 15)
MHV.B5.NcoI   GAA TAG GCC ATG GCG GAG GTC CAG CTG CAA CAA TCT
              (SEQ ID NO: 16)
MHV.B6.NcoI   GAA TAG GCC ATG GCG GAG GTC CAG CTG CAG CAG TC
              (SEQ ID NO: 17)
MHV.B7.NcoI   GAA TAG GCC ATG GCG CAG GTC CAA CTG CAG CAG CCT
              (SEQ ID NO: 18)
MHV.B8.NcoI   GAA TAG GCC ATG GCG GAG GTG AAC CTG GTG GAG TC
              (SEQ ID NO: 19)
MHV.B9.NcoI   GAA TAG GCC ATG GCG GAG GTG AAG CTG GTG GAA TC
              (SEQ ID NO: 20)
MHV.B10.NcoI  GAA TAG GCC ATG GCG GAT GTG AAC TTG GAA GTG TC
              (SEQ ID NO: 21)
MHV.B11.NcoI  GAA TAG GCC ATG GCG GAG GTC CAG CTG CAA CAG TC
              (SEQ ID NO: 22)
MHV.B12.NcoI  GAA TAG GCC ATG GCG GAG GTG CAG CTG GAG GAG TC
              (SEQ ID NO: 23)

Forward primer
MHC.F.HindIII GGC CAG TGG ATA AAC CTT GGG GGT GTC GTT TTG GC
              (SEQ ID NO: 24)

V_L chain:
Back primer
MKV.B1.MluI   TAC AGG ATC CAC GCG TAG ATG TTT TGA TGA CCC AAA CT
              (SEQ ID NO: 25)
MKV.B2.MluI   TAC AGG ATC CAC GCG TAG ATA TTG TGA TGA CGC AGG CT
              (SEQ ID NO: 26)
MKV.B3.MluI   TAC AGG ATC CAC GCG TAG ATA TTG TGA TAA CCC AG
              (SEQ ID NO: 27)
MKV.B4.MluI   TAC AGG ATC CAC GCG TAG ACA TTG TGC TGA CCC AAT CT
              (SEQ ID NO: 28)
MKV.B5.MluI   TAC AGG ATC CAC GCG TAG ACA TTG TGA TGA CCC AGT CT
              (SEQ ID NO: 29)
MKV.B6.MluI   TAC AGG ATC CAC GCG TAG ATA TTG TGC TAA CTC AGT CT
              (SEQ ID NO: 30)
MKV.B7.MluI   TAC AGG ATC CAC GCG TAG ATA TCC AGA TGA CAC AGA CT
              (SEQ ID NO: 31)
MKV.B8.MluI   TAC AGG ATC CAC GCG TAG ACA TCC AGC TGA CTC AGT CT
              (SEQ ID NO: 32)
MKV.B9.MluI   TAC AGG ATC CAC GCG TAC AAA TTG TTC TCA CCC AGT CT
              (SEQ ID NO: 33)
MKV.B10.MluI  TAC AGG ATC CAC GCG TAG ACA TTC TGA TGA CCC AGT CT
              (SEQ ID NO: 34)

Forward primer
MKV.F.Not     TGA CAA GCT TGC GGC CGC GGA TAC AGT TGG TGC AGC ATC
              (SEQ ID NO: 35)
```

A mix consisting of 8 μl First-strand-buffer, 4 μl DTT, 4 μl dNTP, 0.5 μl RnaseInhibitor and 1 μl Dnase was added and further incubated for 30 min at 37° C. Enzymes were deactivated by incubation in 75° C. for 5 minutes. 1 μl reverse transcriptase and 1 μl RnaseInhibitor was added and cDNA was synthesized by incubation with 42° C. for 45 minutes. Heat inactivation occured at 94° C. for 5 minutes.

1.3. PCR-amplification of the variable regions. Amplification was done with the components of the CLONTECH Advantage-high-fidelity Polymerase. The reaction occurred in 50 μl volume with 1 μl of the cDNA (200 pg), 5 μl reaction-buffer, 200 μM of an equimolar mix of dNTP and 25 pmol of the Forward Primer and 25 pmol Backprimer mentioned above. Amplification was done with 36 Cycles, each with denaturation at 94° C. for 15 seconds, annealing at 55° C. to 65° C. for 30 seconds and elongation for 30 second s at 72° C. After the last amplification cycle, one additional elongation for 5 min was added.

1.4. Cloning of the PCR amplified V-regions into the prokaryotic expression vector pOPE-101 (Genbank# Y14585). PCR products, which were amplified with the different annealing temperatures were pooled and DNA was precipitated by the addition of sodiumacetate pH 5.2 (1/10 volume), ethanol (2.5 volume) and 1 μl glycogen (ROCHE) as a carrier. DNA was purified on an 1% agarose gel, excised (QIAGEN Gel purification kit) and either NotI/Mlul (New England Biolabs) digested for the $V_L$ region or NcoI/Hind III (New England Biolabs) for the $V_H$ region. Digestion occurred in 50 μl reaction volume with 45 μl purified DNA (about 2 μg), 5 μl recommended buffer and 5 units of enzyme for 3 hours at 37° C.

Digested DNA was purified by running on a 1% agarose gel and excised from the gel according to the manufactors instructions (QIAGEN Gel purification kit). A 50 ng portion of the digested and gel-purified $V_L$ region was ligated with 500 ng of the appropriately digested and purified expression vector pOPE101 in a final volume of 40 μl with 1 μl ligase (Boeringer Mannheim) at 16° C. overnight. DNA was precipitated, electroporated in XL 1 blue (Epicurian coli; STRATAGENE), and bacteria were grown for 1 h in 1 ml SOC-medium to allow recuperation. Bacteria were plated on $SOB_{GAT}$ plates (0.1 M glucose, 100 μg·ml$^{-1}$ ampicillin, 12.5 μg·ml$^{-1}$, tetracycline), and, after overnight incubation, clones were scaped off and DNA was isolated with a DNA purification column according to the manufactors instructions (MACH-EREY and NAGEL).

Vector DNA (containing the $V_L$ chain) was digested with NcoI/HindIII, purified by running on a 1% agarose gel and excised from the gel according to the manufactors instructions (QIAGEN Gel purification kit).

Ligation of this purified and digested vector DNA with the NcoI/HindIII digested $V_H$-regions mentioned above was done as described. After electroporation in E. coli independent clones were picked and screened for the expression of functional scFv (single-chains) with specificity against Peptide.

1.5. Screening of the transfected bacteria for positive binders. Bacterial expression was IPTG-induced and soluble scFv-myc fusionprotein was rescued from the periplasmatic compartment by osmotic lysis of the bacteria. Supernatant containing the scFv-myc fusionprotein was blocked in 2% Milk PBS and incubated for 3 h in wells of an ELISA-Plate previously coated with 100 ng peptide/well. Detection of Peptid6-bound scFv was done by incubation with anti-c-myc (mouse) and Horseradish-peroxidase conjugated anti-mouse (rabbit). Vector DNA of positive clones were rescued and the $V_H$ and $V_L$ regions nucleotide sequences were determined. Sequences of the $V_H$ and $V_L$ regions are depicted in FIGS. 1 and 2. Furthermore, nucleotide sequences encoding $V_H$ and $V_L$ regions from am allelic variant of clone 17 have been isolated. Those sequences are depicted in FIGS. 9 ($V_H$) and 10 ($V_L$). The nucleotide and amino acid sequences of said allelic variants are substantially identical with those of the variable region comprising the amino acid sequence shown in FIGS. 1 and 2, except in the $V_H$ chain at amino acid position 1 (E→Q), 5 (Q→K) and in the $V_L$ at amino acid position 1 (Q→D). Antibodies comprising said variable regions have been tested and shown to display the binding and functional characteristics described in section 2.2, infra. Furthermore, those antibodies have been shown to be biologically and therapeutically active in accordance with the experiments described in Examples 3 to 11.

2. Construction of Chimeric Antibody

For the construction of the chimeric recombinant antibody, the $V_H$ and $V_L$ variable regions were either cloned into the pConGamma1f-vector (for the $V_H$ region) or into the pConKappa-vector (for the $V_L$ region) purchased by LONZA Biologics, (Slough, UK). Thereby, upstream of the variable regions a IgG-leadersequence and a Kozak-sequence was introduced for secretion into the medium. The two vectors (pConGamm1f and pConKappa) had been fused in order to facilitate transfection and to achieve a balanced production of light and heavy chains.

2.1. Introduction of the eukaryotic leader sequence by PCR: components of the CLONTECH Advantage-high-fidelity Polymerase had been used. The PCR reaction occurred in 50 µl volume with 1 µl (100 ng) of the pOPE vector containing either the $V_H$ or the $V_L$ region as a template, 5 µl reaction-buffer, 200 µM of an equimolar mix of dNTP and 25 pmol of the Forward Primer and 25 pmol Backprimer mentioned below.

Primer for the introduction of the leader sequence and cloning of the V-regions:

A: cloning of the $V_H$ chain in the pConGamma1f Vector:

```
5'-primer:
5'#9LeaderVH-HindIII:  5'- GCG CGC AAG CTT GCC GCC ACC ATG GGA TGG
                       AGC TGT ATC ATC CTC TTC TTG GTA GCA ACA GCT
                       ACA GGT GTC CAC TCC GAG GTG CAG CTG CAA CAG
                       TC-3'
                       (SEQ ID NO: 36)

3'-primer:
3'#9VH-ApaI:           5'- TTT ATA TGG GCC CTT GGT GGA GGC TGA GGA
                       GAC GGT GAC CGT GGT-3'
                       (SEQ ID NO: 37)
```

B: cloning of the $V_H$-chain in the pConKappa Vector:

```
5'-primer:
5'#9LeaderVL-HindIII:      5'- GCG CGC AAG CTT GCC GCC ACC ATG GGA TGG
                           AGC TGT ATC ATC CTC TTC TTG GTA GCA ACA GCT
                           ACA GGT GTC CAC TCC CAA ATT GTT CTC ACC CAG
                           TCT -3'
                           (SEQ ID NO: 37)

3'primer:
3'#9VL BsiWI:              5'- ATA TGG CGT ACG TTT GAT TTC CAA CTT GGT
                           GCC-3'
                           (SEQ ID NO: 38)

auxilliary primer for the 5' primer:
HindIII-Kozakbeg:          5'- GCG CGC AAG CTT GCC GCC AC -3'
                           (SEQ ID NO: 12)
```

Amplification was done with 36 Cycles, each with denaturation at 94° C. for 15 seconds, annealing at 65° C. for 30 seconds and elongation for 30 seconds at 72° C. After the 10$^{th}$ cycle, 25 pmol of the primer HindIII-Kozakbeg had been added to the reaction mix. After the last amplification cycle, one additional elongation period for 5 min was added.

2.2. Cloning into vectors containing the IgG-constant region. The PCR product was purified by running on a 1% agarose gel, digested with HindIII/ApaI ($V_H$ chain) or Hind III/BsiWI ($V_L$ chain) and again gel purified. 50 ng of the digested $V_H$ and $V_L$ regions were ligated into 200 ng of the appropriately digested pConGamma1f and pConKappa vectors, respectively. The $V_H$ expression cassette, containing the promoter-region and the gene for the entire Heavy chain, was rescued from the pConGamma1f-vector by digestion with NotI/SalI and ligated in the appropriately digested and purified pConKappa vector. The resulted double gene vector was linearized with Pvu I, phenol/chloroform extracted and 1 µg was used for the transfection of either 1×10$^7$ NSO or CHO cells.

Antibody was isolated and tested for binding and biological activity. The binding and functional characteristics of the chimeric antibodies as compared to the murine antibodies and can be summarized as follows:

ELISA: -Specificity for the TIRC7 derived peptide Peptid6

WesternBlot: -Same band pattern as the murine mAb

T cell proliferation assay: -Inhibition of mitogen induced T cell proliferation

Affinity of chimeric Neliximab against peptide 6: Kd=1 nM

Affinity of murine Neliximab against peptide 6: Kd=1 nM

Example 3

Further Functional Characterization of Antibody Clone #17 (Murine Neliximab)

Stable antibody producing hybridomas were generated according to the PEG-fusion technique, spleen cells of immunized BALB/c-mice being fused with SP2/0-Ag14 (ATCC) myeloma cells. A purified, murine version of the mAb Neliximab was tested in several functional assays to analyse its potential immunomodulatory properties.

The standard in vitro test of biological function is a proliferation assay. Briefly, the influence of murine Neliximab on the proliferation rate of mitogenic (PHA) and alloantigen stimulated, human PBMC (peripheral mononuclear cells), which were isolated from fresh blood of healthy donors according to the ficoll-centrifugation protocol, was determined in comparison to an appropriate murine isotype control. Proliferation of PBMC co-cultured in vitro with either TIRC7 or isotype control antibody was quantified by scintillation counting of incorporated $^3$H-thymidine into the proliferating cells.

Cytokine expression was also routinely determined. Supernatant of co-cultured stimulated, human PBMC was harvested after 48 h and used for quantification of the two $T_H1$-cytokines IFNγ and IL-2, and the two $T_H2$-cytokines IL-4 and IL-10 by ELISA employing dilutions of known cytokine concentrations as standards. In each case, cytokine secretion was compared to that of an appropriate isotype control.

Some of the functional data are reported in the following tables and example 5 and are discussed further below. For completeness, the results of the remaining assays are summarized briefly here.

The proliferation of PHA-stimulated human PBMC was significantly inhibited in a dose dependent manner by murine anti-human TIRC7 mAb using $^3$H-thymidine and BrdU incorporation and detection. The specificity of the inhibitory effect of murine anti-human TIRC7 mAb on the proliferation of PHA-stimulated human PBMC was proven by reversal of the inhibitory effect through pre-incubation of the antibody with its respective peptide due to blockade of the antigen binding regions of the antibody.

The in vitro co-incubation of murine Neliximab with separated CD4$^+$ and CD8$^+$ human T cells revealed a significant inhibitory effect on the proliferation of PHA and IL-2 stimulated CD4$^+$ but only a moderate effect on CD8$^+$ T cells compared to an appropriate isotype control.

The secretion of the $T_H1$-cytokines IFNγ (Table 1) and IL-2 (Table 2) was reduced in a highly significant, dose-dependent manner by murine anti-human TIRC7 mAb.

TABLE 1

Effect of murine Neliximab on IFNγ-secretion of co-incubated, PHA-stimulated, human PBMC in vitro (n = 18, mean ± SD).

| Concentration of murine Neliximab (µg/ml) | Inhibition of cytokine secretion calculated relative to the isotype control at the same concentration (% ± SD) |
|---|---|
| 10 | 78 ± 12 (p = 0.002) |
| 50 | 39 ± 8 (p = 4.95E−11) |
| 100 | 20 ± 2 (p = 2.86E−20) |
| 200 | 3 ± 1 (p = 2.34E−17) |

Supernatants of co-cultured cells were harvested after 48 h and cytokine concentrations were determined by ELISA. Murine Neliximab inhibited IFNγ-secretion of mitogenic stimulated cells in vitro in a significant and dose-dependent manner. When calculated by logarithmical regression analysis, the inhibitory dosage causing a 50% reduction in cytokine secretion ($ID_{50}$) was 31.0 µg/ml (r = 0.9991).

TABLE 2

Effect of murine Neliximab on IL-2-secretion of co-incubated, PHA-stimulated, human PBMC in vitro (n = 6, mean ± SD).

| Concentration of murine Neliximab (µg/ml) | Inhibition of cytokine secretion calculated relative to the isotype control at the same concentration (% ± SD) |
|---|---|
| 10 | 113 ± 22 (p = 1.43E−07) |
| 50 | 18 ± 3 (p = 1.08E−05) |
| 100 | 11 ± 5 (p = 0.500) |

Supernatants of co-cultured cells were harvested after 48 h and cytokine concentrations were determined by ELISA. Murine Neliximab caused a significant, dose-dependent inhibition of IL-2-secretion of mitogenic stimulated cells in vitro. The $ID_{50}$ (calculated by logarithmical regression analysis) was 34.8 µg/ml (r = 0.9452).

By contrast, no effect was observed on the production of the cytokines TNFα, IL-1 and IL-12.

The secretion of the $T_H2$-cytokines IL-4 (Table 3) and IL-10 (Table 4) was also not affected by co-incubation with murine anti-human TIRC7 mAb in comparison to an appropriate murine control.

TABLE 3

Effect of murine Neliximab on IL-4-secretion
of co-incubated, PHA-stimulated, human PBMC
in vitro (n = 10, mean ± SD).

| Concentration of murine Neliximab (µg/ml) | Inhibition of cytokine secretion calculated relative to the isotype control at the same concentration (% ± SD) |
|---|---|
| 10 | 100 ± 5 (p = 0.994) |
| 50 | 87 ± 19 (p = 0.779) |
| 100 | 88 ± 7 (p = 0.776) |

Supernatants of co-cultured cells were harvested after 48 h and cytokine concentrations were determined by ELISA. IL-4-secretion of PHA-stimulated, human PBMC was not significantly affected by co-incubation with murine Neliximab in vitro relative to an appropriate murine isotype control.

TABLE 4

Effect of murine Neliximab on IL-10-secretion
of co-incubated, PHA-stimulated, human PBMC
in vitro (n = 12, mean ± SD)

| Concentration of murine Neliximab (µg/ml) | Inhibition of cytokine secretion calculated relative to the isotype control at the same concentration (% ± SD) |
|---|---|
| 10 | 102 ± 6 (p = 0.936) |
| 50 | 90 ± 6 (p = 0.501) |
| 100 | 106 ± 8 (p = 0.647) |

Supernatants of co-cultured cells were harvested after 48 h and cytokine concentrations were determined by ELISA. IL-10-secretion of PHA-stimulated, human PBMC was not significantly affected by co-incubation with murine Neliximab in vitro relative to an appropriate murine isotype control.

On the basis of the above findings, it may be concluded that murine Neliximab influences the immune response at an early stage in vitro, preferentially by inhibition of the $T_H1$-immune response without affecting the secretion of $T_H2$-cytokines.

Example 4

Functional Characterization of Chimeric Neliximab

Using the protocol described above for the proliferation assay with murine anti-human TIRC7 mAb (murine Neliximab), the chimeric antibody, Neliximab, was investigated with respect to its potential impact on the proliferation rate of PHA-stimulated, human PBMC in vitro. It was found that Neliximab inhibited cell proliferation significantly in a dose-dependent manner. Similarly, quantification of IFNγ in cell culture supernatants after 48 h of co-culture with Neliximab showed a significant, dose-dependent inhibition of cytokine secretion (see Tables 5 and 6).

TABLE 5

Effect of Neliximab (chimeric anti-human TIRC7 mAB)
on IFNγ-secretion of co-cultivated, PHA-stimulated,
human PBMC in vitro (n = 12, mean ± SD)

| Concentration of Neliximab (µg/ml) | Inhibition of cytokine secretion calculated relative to the positive control (% ± SD) |
|---|---|
| 100 | 114 ± 7 (p = 0.841) |
| 200 | 20 ± 3 (p = 2.95E–09) |
| 400 | 6 ± 2 (p = 2.09E–13) |

Cytokine concentrations were quantified by ELISA. Neliximab inhibited IFNγ-production of mitogenic stimulated cells in vitro in a significant, dose-dependent manner. The $ID_{50}$ (calculated by logarithmical regression analysis) was 191.5 µg/ml (r = 0.8454).

TABLE 6

Effect of Neliximab (chimeric anti-human TIRC7
mAb) on proliferation rate of mitogenic stimulated
cells in vitro (n = 9, mean ± SD)

| Concentration of Neliximab (µg/ml) | Inhibition of proliferation rate calculated relative to the positive control (% ± SD) |
|---|---|
| 100 | 58 ± 2 (p = 0.005) |
| 200 | 36 ± 3 (p = 1.35E–04) |
| 400 | 8 ± 2 (p = 4.96E–06) |

Proliferation rate was measured by $^3$H-thymidine-incorporation. Neliximab inhibited the proliferation rate of mitogenic stimulated cells in vitro in a significant, dose-dependent manner. The $ID_{50}$ (calculated by logarithmical regression analysis) was 128.5 µg/ml (r = 0.9952).

Example 5

Functional In Vivo Assays with Murine Neliximab

Murine Neliximab cross-reacted with murine and rat TIRC7. Therefore in vivo activation studies with polyclonal and monoclonal anti-human TIRC7 Abs were performed. The functional activity of anti-human TIRC7 mAbs in two in vivo model systems is described below.

Example 6

Collagen Induction Model in Mice

The functional effect of murine anti-human TIRC7 mAb was studied in a collagen induction model in mice using either therapeutic treatment or preventive treatment. The murine model of collagen type II induced arthritis has similarities to rheumatoid arthritis (RA) in its marked MHC class II predisposition, as well as in histology, immunohistology, erosions of cartilage and bone, and in its response to anti-TNF therapy. Thus the animal model serves as a good approximation to human disease. The model of rheumatoid arthritis used herein is described for examlpe by Williams et al., Proc. Natl. Acad. Sci. USA 89 (1992), 9784-9788, i.e. the collagen type II induced arthritis in the DBA/1 mouse. Type II collagen can be purified from bovine articular cartilage by limited pepsin solubilization and salt fractionation as described for example by Miller, Biochemistry 11 (1972),4903-4909.

Example 7

Therapeutic Treatment

The effect of modulating the TIRC7-mediated signal was studied in an animal model of rheumatoid arthritis, collagen-induced arthritis (CIA), using a therapeutic treatment regimen. Three groups of 8 week-old male DBA/1 mice (Charles River, Germany) were immunized intradermally at the base of the tail with bovine Collagen Type II (CII, 100 µg, Sigma, St. Louis) emulsified in complete Freund's adjuvant (CFA, Sigma). Mice were rechallenged with CII in incomplete Freund's adjuvant (IFA, Sigma) 21 days later. Two groups of animals with different treatment regimens were used: one group of mice (n=7) was given murine Neliximab in a therapeutic regimen (500 µg starting on day 24 three times per week) and one group was untreated (n=7).

CIA development was inspected daily for signs of joint inflammation of the four paws and was graded in the following arthritic scores: 0, no signs of erythema and swelling; 1, erythema of digits or swelling of metacarpal or metatarsal joints; 2, erythema and mild swelling of digits and/or metacarpal or metatarsal joints; 3, erythema and severe swelling of digits and metacarpal or metatarsal joints; 4, paws with deformity or ankylosis. The maximum arthritic score per paw was 4, and the maximum disease score per mouse was 16.

The main findings may be summarised as follows (see FIG. 3). Arthritic symptoms consisting of erythema and swelling of digits, carpal and metatarsal regions became clinically evident around 22 days after immunization. Mice in the non treated control group developed typical clinical symptoms of moderate to severe arthritis, which started at about day 22 and progressed rapidly to a mean arthritic score of 12 at the end of the study. However, relative to the control group, the therapeutic group showed a much slower progression in the development of clinical symptoms and reached a significantly lower mean arthritic score of 2.5 at the end of the study.

On the basis of these findings in mice, it may be concluded that murine Neliximab significantly improves the clinical score in the therapeutic treatment of CIA in vivo.

Example 8

Preventive Treatment

The effect of modulating the TIRC7-mediated signal was also studied in CIA using a preventive treatment regimen. As in Example 7, DBA/1 mice were immunized with bovine CII in complete Freund's adjuvant (CFA). After 21 days, the animals were challenged again with incomplete Freund's adjuvant (IFA). The treated group of mice (n=7) was given anti-TIRC7 mAbs in a preventive treatment regimen (250 µg starting on day 0, 0.5 hr before and 2 hr after the immunization, and thereafter 250 µg daily from day 1-6), while the control group received no treatment (n=7).

Development of CIA was assessed and scored in exactly the same way as in the therapeutic treatment study.

The main findings may be summarised as follows (see FIG. 4). Arthritic symptoms consisting of erythema and swelling of digits, carpal and metatarsal regions became clinically evident around 22 days after immunization. Mice in the control group developed typical clinical symptoms of moderate to severe arthritis, which started at about day 22 and progressed rapidly to a mean arthritic score of 14 at the end of the study. By contrast, in mice treated with murine Neliximab prior to the onset of disease, arthritic symptoms were not manifested until about day 60 and the progression of arthritis was substantially inhibited, reaching a mean score of 1 towards the end of the study period (day 80).

On the basis of these findings in an in vivo mice model, it may be concluded that murine Neliximab significantly delays the onset of arthritis in preventive treatment of CIA.

Example 9

Cardiac Allograft Rejection in Mice

Cardiac allograft survival time was studied in mice. Briefly, hearts from C57/BL10 (H2$^b$) mice were transplanted into CBA (H$_2$k) recipients. Recipient mice in the treated group were administered anti-TIRC7 mAb (1 mg) intravenously, 2 h before, directly after and daily from d1 to d5 after transplantation. Mice in the control group were given only the vehicle. The graft function was assessed by daily palpation, and the day of rejection was determined as the day of cessation of heart beat. (In preliminary studies not reported here, the grafts were harvested and splenocytes isolated 7 days after transplantation. The transplanted tissue was analyzed by histology. The alteration of several surface markers such as CD25, CD28 and CTLA-4 in splenocytes were analyzed using flow cytometry.)

The main findings may be summarised as follows (see FIG. 5). The mean graft survival time in the group treated with murine Neliximab was 52 days. The longest survival time observed to date was over 120 days. By contrast, the mean graft survival time in the control group was only 8 days. Preliminary results of the histological analysis indicate far less mononuclear cell infiltration in the treated group than in the control group.

On the basis of these findings, it may be concluded that murine Neliximab prolongs the graft survival time in an acute cardiac allograft rejection model in mice.

Example 10

Therapeutic Activity of Neliximab in Comparison to Enbrel (TNF-α Antagonist) in RA Mice Model Mice were treated as described in Example 7 except that Neliximab was used at a concentration of 500 µg, Enbrel at 50 µg and a combination of Neliximab and Enbrel with 250 µg Neliximab and 25 µg Enbrel. Thus, the combination group received only 250 µg of Neliximab and 25 µg of Enbrel whereas the Neliximab group alone was treated with 500 µg and Enbrel alone was treated with 50 µg pro day. The treatment regimen is shown in FIG. 6. It could be surprisingly shown that Neliximab alone or in combination with Enbrel shows significant therapeutic activity in RA mice model in comparison to Enbrel and control antibody treated and non-treated mice. In particular, the synergistic effect when using Neliximab and Enbrel together at half of their concentration compared to the corresponding monotherapy was unexpected. However, besides the improvement of the clinical score in the therapeutic treatment of CIA it could be surprisingly be shown that when the individual animals of each group were analyzed, the number of non-responder in the combination therapy was less than could be expected from each individual group; see FIG. 7. Thus, treatment with both Neliximab and Enbrel is efficacious for subjects which do not respond to either of those drugs alone.

On the basis of these findings in an in vivo mice model, it is reasonable to conclude that therapy of inflammatory diseases with TIRC7 antagonist such as anti-TIRC7 antibodies in conjunction with other anti-inflammatory drugs opens up a way for the treatment of patients which hitherto have not been amenable to therapeutic treatment.

Example 11

Functional Characterization of Chimeric Neliximab in Comparison to Enbrel (TNF-α Antagonist)

Mice were treated as described in Example 7 except that Neliximab was used at a concentration of 500 µg and Enbrel at a concentration of 50 µg. Splenocytes of one representative animal of each group with clinical score of 2 (Nelix and Enbrel) and 4 (control mAb) were isolated 70 days after disease induction and 5 weeks treatment. Splenocytes were activated with LPS for 48 h and supernatant of activated splenocytes as well as control cells was analysed for the expression of different cytokines with ELISA. It could be shown that Neliximab (Nelix) down regulates IL-6 expression after ex vivo LPS stimulation of splenocytes whereas no changes were observed in TNF-α expression in comparison to Enbrel and control antibody. In addition, Neliximab down regulates IFN-γ expression after ex vivo PHA stimulation of splenocytes whereas no changes were observed in IL-2 and IL-10 expression in contrast to Enbrel; see FIG. 8. Furthermore, experiments with 48 h PHA-activated splenocytes revealed that long term treatment with Neliximab and Enbrel does not affect T cell proliferation in response to mitogen.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention claimed by the claims.

The invention claimed is:

1. An anti-TIRC7 antibody or antigen binding fragment thereof comprising all three complementarity determining regions (CDRs) of the $V_H$ and all three complementarity determining regions (CDRs) of the $V_L$ variable regions, wherein the amino acid sequences of said $V_H$ and $V_L$ variable regions are set forth in (a) SEQ ID NO:2 and SEQ ID NO:4, respectively; or (b) SEQ ID NO:9 and SEQ ID NO:11, respectively.

2. The antibody of claim 1, wherein said antibody is a chimeric or humanized antibody.

3. The antibody of claim 1 comprising the amino acid sequence of the $V_H$ and $V_L$ variable regions set forth in SEQ ID NO:2 and SEQ ID NO: 4, respectively; or SEQ ID NO: 9 and SEQ ID NO: 11, respectively.

4. A composition comprising the antibody of claim 1, optionally in combination with a pharmaceutically acceptable carrier.

* * * * *

SEQUENCE LISTING

<160> NUMBER OF SEQ ID NOS: 42

<210> SEQ ID NO 1
<211> LENGTH: 396
<212> TYPE: DNA
<213> ORGANISM: Mus musculus
<220> FEATURE:
<221> NAME/KEY: CDS
<222> LOCATION: (1)..(396)

<400> SEQUENCE: 1

```
gag gtc cag ctg cag cag tct gga ccg gag ctg gta aag cct ggg gct        48
Glu Val Gln Leu Gln Gln Ser Gly Pro Glu Leu Val Lys Pro Gly Ala
1               5                   10                  15 tca gtg aag atg tcc tgc aag gct tct ggg tac act ttc act acc tat        96
Ser Val Lys Met Ser Cys Lys Ala Ser Gly Tyr Thr Phe Thr Thr Tyr
            20                  25                  30 gtt atg cac tgg gtg aag cag aag cct ggg cag ggc ctt gag tgg att       144
Val Met His Trp Val Lys Gln Lys Pro Gly Gln Gly Leu Glu Trp Ile
        35                  40                  45 gga tat att aat cct tac aat gat ggt act aac tac aat gag aag ttc       192
Gly Tyr Ile Asn Pro Tyr Asn Asp Gly Thr Asn Tyr Asn Glu Lys Phe
    50                  55                  60 aaa ggc aag gcc aca ctg acc tca gac aaa tcc tcc agt aca gcc tac       240
Lys Gly Lys Ala Thr Leu Thr Ser Asp Lys Ser Ser Ser Thr Ala Tyr
65                  70                  75                  80 atg gag ctc agc acc ctg acc tct gag gac tct gcg gtc tat tac tgt       288
Met Glu Leu Ser Thr Leu Thr Ser Glu Asp Ser Ala Val Tyr Tyr Cys
                85                  90                  95 gcg gaa ttt att act aag aca gtc ggt ggg tcc aac tgg tac ctc gat       336
Ala Glu Phe Ile Thr Lys Thr Val Gly Gly Ser Asn Trp Tyr Leu Asp
            100                 105                 110 gtc tgg ggc gca ggg acc acg gtc acc gtc tcc tca gcc aaa acg aca       384
Val Trp Gly Ala Gly Thr Thr Val Thr Val Ser Ser Ala Lys Thr Thr
        115                 120                 125 ccc cca aag ctt                                                        396
Pro Pro Lys Leu
    130
```

<210> SEQ ID NO 2
<211> LENGTH: 132
<212> TYPE: PRT
<213> ORGANISM: Mus musculus

<400> SEQUENCE: 2

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Thr Tyr
            20                  25                  30

Val Met His Trp Val Lys Gln Lys Pro Gly Gln Gly Leu Glu Trp Ile
        35                  40                  45
```

-continued

```
Gly Tyr Ile Asn Pro Tyr Asn Asp Gly Thr Asn Tyr Asn Glu Lys Phe
    50                  55                  60
Lys Gly Lys Ala Thr Leu Thr Ser Asp Lys Ser Ser Ser Thr Ala Tyr
 65                  70                  75                  80
Met Glu Leu Ser Thr Leu Thr Ser Glu Asp Ser Ala Val Tyr Tyr Cys
                 85                  90                  95
Ala Glu Phe Ile Thr Lys Thr Val Gly Gly Ser Asn Trp Tyr Leu Asp
            100                 105                 110
Val Trp Gly Ala Gly Thr Thr Val Thr Val Ser Ser Ala Lys Thr Thr
        115                 120                 125
Pro Pro Lys Leu
    130
```

<210> SEQ ID NO 3
<211> LENGTH: 354
<212> TYPE: DNA
<213> ORGANISM: Mus musculus
<220> FEATURE:
<221> NAME/KEY: CDS
<222> LOCATION: (1)..(354)

<400> SEQUENCE: 3

```
caa att gtt ctc acc cag tct cca gca atc atg tct gct tct cca ggg       48
Gln Ile Val Leu Thr Gln Ser Pro Ala Ile Met Ser Ala Ser Pro Gly
 1               5                  10                  15
gag aag gtc acc atg acc tgc agt gcc agc tca agt ata agt tac ata       96
Glu Lys Val Thr Met Thr Cys Ser Ala Ser Ser Ser Ile Ser Tyr Ile
            20                  25                  30
cac tgg ttc caa cag aag cca ggc acc tcc ccc aaa aga tgg att tat      144
His Trp Phe Gln Gln Lys Pro Gly Thr Ser Pro Lys Arg Trp Ile Tyr
        35                  40                  45
gac aca tcc aaa ctg cct tct gga gtc cct gct cgc ttc agt ggc agt      192
Asp Thr Ser Lys Leu Pro Ser Gly Val Pro Ala Arg Phe Ser Gly Ser
    50                  55                  60
ggg tct ggg acc tct tat tct ctc aca atc agc agc atg gag gct gaa      240
Gly Ser Gly Thr Ser Tyr Ser Leu Thr Ile Ser Ser Met Glu Ala Glu
 65                  70                  75                  80
gat gct gcc act tat tac tgc cat cag cgg agt agt tac acg tgg acg      288
Asp Ala Ala Thr Tyr Tyr Cys His Gln Arg Ser Ser Tyr Thr Trp Thr
                 85                  90                  95
ttc ggt gga ggc acc aag ctg gaa atc aaa cgg gct gat gct gca cca      336
Phe Gly Gly Gly Thr Lys Leu Glu Ile Lys Arg Ala Asp Ala Ala Pro
            100                 105                 110
act gta tcc gcg gcc gcc                                              354
Thr Val Ser Ala Ala Ala
        115
```

<210> SEQ ID NO 4
<211> LENGTH: 118
<212> TYPE: PRT
<213> ORGANISM: Mus musculus

<400> SEQUENCE: 4

```
Gln Ile Val Leu Thr Gln Ser Pro Ala Ile Met Ser Ala Ser Pro Gly
 1               5                  10                  15
Glu Lys Val Thr Met Thr Cys Ser Ala Ser Ser Ser Ile Ser Tyr Ile
            20                  25                  30
His Trp Phe Gln Gln Lys Pro Gly Thr Ser Pro Lys Arg Trp Ile Tyr
        35                  40                  45
Asp Thr Ser Lys Leu Pro Ser Gly Val Pro Ala Arg Phe Ser Gly Ser
```

```
                50                  55                  60
Gly Ser Gly Thr Ser Tyr Ser Leu Thr Ile Ser Ser Met Glu Ala Glu
 65                  70                  75                  80

Asp Ala Ala Thr Tyr Tyr Cys His Gln Arg Ser Ser Tyr Thr Trp Thr
                 85                  90                  95

Phe Gly Gly Gly Thr Lys Leu Glu Ile Lys Arg Ala Asp Ala Ala Pro
            100                 105                 110

Thr Val Ser Ala Ala Ala
        115

<210> SEQ ID NO 5
<211> LENGTH: 24
<212> TYPE: PRT
<213> ORGANISM: Artificial Sequence
<220> FEATURE:
<223> OTHER INFORMATION: TIRC7 peptide 7c

<400> SEQUENCE: 5

Asp Leu Pro Asp Ala Ser Val Asn Gly Trp Ser Ser Asp Glu Glu Lys
 1               5                  10                  15

Ala Gly Gly Leu Asp Asp Glu Glu
            20

<210> SEQ ID NO 6
<211> LENGTH: 14
<212> TYPE: PRT
<213> ORGANISM: Artificial Sequence
<220> FEATURE:
<223> OTHER INFORMATION: TIRC7 peptide 6

<400> SEQUENCE: 6

Asp Leu Pro Asp Ala Ser Val Asn Gly Trp Ser Ser Asp Glu
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: Peptide of soluble fibronectin

<400> SEQUENCE: 7

Gly Pro Glu Ile Leu Asp Val Pro Ser Thr
 1               5                  10

<210> SEQ ID NO 8
<211> LENGTH: 372
<212> TYPE: DNA
<213> ORGANISM: Mus musculus
<220> FEATURE:
<221> NAME/KEY: CDS
<222> LOCATION: (1)..(372)

<400> SEQUENCE: 8 cag gtg cag ctg aag cag tct gga ccg gag ctg gta aag cct ggg gct      48
Gln Val Gln Leu Lys Gln Ser Gly Pro Glu Leu Val Lys Pro Gly Ala
 1               5                  10                  15 tca gtg aag atg tcc tgc aag gct tct ggg tac act ttc act acc tat      96
Ser Val Lys Met Ser Cys Lys Ala Ser Gly Tyr Thr Phe Thr Thr Tyr
            20                  25                  30 gtt atg cac tgg gtg aag cag aag cct ggg cag ggc ctt gag tgg att     144
Val Met His Trp Val Lys Gln Lys Pro Gly Gln Gly Leu Glu Trp Ile
        35                  40                  45
```

```
gga tat att aat cct tac aat gat ggt act aac tac aat gag aag ttc      192
Gly Tyr Ile Asn Pro Tyr Asn Asp Gly Thr Asn Tyr Asn Glu Lys Phe
    50                  55                  60 aaa ggc aag gcc aca ctg acc tca gac aaa tcc tcc agt aca gcc tac      240
Lys Gly Lys Ala Thr Leu Thr Ser Asp Lys Ser Ser Ser Thr Ala Tyr
65                  70                  75                  80 atg gag ctc agc acc ctg acc tct gag gac tct gcg gtc tat tac tgt      288
Met Glu Leu Ser Thr Leu Thr Ser Glu Asp Ser Ala Val Tyr Tyr Cys
                85                  90                  95 gcg gaa ttt att act aag aca gtc ggt ggg tcc aac tgg tac ctc gat      336
Ala Glu Phe Ile Thr Lys Thr Val Gly Gly Ser Asn Trp Tyr Leu Asp
                100                 105                 110 gtc tgg ggc gca ggg acc acg gtc acc gtc tcc tca                      372
Val Trp Gly Ala Gly Thr Thr Val Thr Val Ser Ser
            115                 120
```

<210> SEQ ID NO 9
<211> LENGTH: 124
<212> TYPE: PRT
<213> ORGANISM: Mus musculus

<400> SEQUENCE: 9

```
Gln Val Gln Leu Lys Gln Ser Gly Pro Glu Leu Val Lys Pro Gly Ala
1               5                   10                  15

Ser Val Lys Met Ser Cys Lys Ala Ser Gly Tyr Thr Phe Thr Thr Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Asn Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Thr Leu Thr Ser Glu Asp Ser Ala Val Tyr Tyr Cys
                85                  90                  95

Ala Glu Phe Ile Thr Lys Thr Val Gly Gly Ser Asn Trp Tyr Leu Asp
                100                 105                 110

Val Trp Gly Ala Gly Thr Thr Val Thr Val Ser Ser
            115                 120
```

<210> SEQ ID NO 10
<211> LENGTH: 318
<212> TYPE: DNA
<213> ORGANISM: Mus musculus
<220> FEATURE:
<221> NAME/KEY: CDS
<222> LOCATION: (1)..(318)

<400> SEQUENCE: 10

```
gat att gtg cta act cag tct cca gca atc atg tct gct tct cca ggg       48
Asp Ile Val Leu Thr Gln Ser Pro Ala Ile Met Ser Ala Ser Pro Gly
1               5                   10                  15 gag aag gtc acc atg acc tgc agt gcc agc tca agt ata agt tac ata       96
Glu Lys Val Thr Met Thr Cys Ser Ala Ser Ser Ser Ile Ser Tyr Ile
            20                  25                  30 cac tgg ttc caa cag aag cca ggc acc tcc ccc aaa aga tgg att tat      144
His Trp Phe Gln Gln Lys Pro Gly Thr Ser Pro Lys Arg Trp Ile Tyr
        35                  40                  45 gac aca tcc aaa ctg cct tct gga gtc cct gct cgc ttc agt ggc agt      192
Asp Thr Ser Lys Leu Pro Ser Gly Val Pro Ala Arg Phe Ser Gly Ser
    50                  55                  60
```

```
ggg tct ggg acc tct tat tct ctc aca atc agc agc atg gag gct gaa    240
Gly Ser Gly Thr Ser Tyr Ser Leu Thr Ile Ser Ser Met Glu Ala Glu
65              70                  75                  80 gat gct gcc act tat tac tgc cat cag cgg agt agt tac acg tgg acg    288
Asp Ala Ala Thr Tyr Tyr Cys His Gln Arg Ser Ser Tyr Thr Trp Thr
                85                  90                  95 ttc ggt gga ggc acc aag ctg gaa atc aaa                            318
Phe Gly Gly Gly Thr Lys Leu Glu Ile Lys
            100                 105

<210> SEQ ID NO 11
<211> LENGTH: 106
<212> TYPE: PRT
<213> ORGANISM: Mus musculus

<400> SEQUENCE: 11

Asp Ile Val Leu Thr Gln Ser Pro Ala Ile Met Ser Ala Ser Pro Gly
1               5                   10                  15

Glu Lys Val Thr Met Thr Cys Ser Ala Ser Ser Ile Ser Tyr Ile
            20                  25                  30

His Trp Phe Gln Gln Lys Pro Gly Thr Ser Pro Lys Arg Trp Ile Tyr
        35                  40                  45

Asp Thr Ser Lys Leu Pro Ser Gly Val Pro Ala Arg Phe Ser Gly Ser
    50                  55                  60

Gly Ser Gly Thr Ser Tyr Ser Leu Thr Ile Ser Ser Met Glu Ala Glu
65              70                  75                  80

Asp Ala Ala Thr Tyr Tyr Cys His Gln Arg Ser Ser Tyr Thr Trp Thr
                85                  90                  95

Phe Gly Gly Gly Thr Lys Leu Glu Ile Lys
            100                 105

<210> SEQ ID NO 12
<211> LENGTH: 20
<212> TYPE: DNA
<213> ORGANISM: Artificial Sequence
<220> FEATURE:
<223> OTHER INFORMATION: 5' primer for cloning VH chain of murine
      anti-Tirc7 antibody in the pConKappa vector

<400> SEQUENCE: 12
gcgcgcaagc ttgccgccac                                              20

<210> SEQ ID NO 13
<211> LENGTH: 35
<212> TYPE: DNA
<213> ORGANISM: Artificial Sequence
<220> FEATURE:
<223> OTHER INFORMATION: Back primer for amplification of murine
      variable regions, VH chain, of anti-Tirc7 antibody

<400> SEQUENCE: 13
gaataggcca tggcgcaggt gcagctgaag gagtc                             35

<210> SEQ ID NO 14
<211> LENGTH: 35
<212> TYPE: DNA
<213> ORGANISM: Artificial Sequence
<220> FEATURE:
<223> OTHER INFORMATION: Back primer for amplification of murine
      variable regions, VH chain, of anti-Tirc7 antibody

<400> SEQUENCE: 14
gaataggcca tggcgcaggt gcagctgaag cagtc                             35
```

<210> SEQ ID NO 15
<211> LENGTH: 35
<212> TYPE: DNA
<213> ORGANISM: Artificial Sequence
<220> FEATURE:
<223> OTHER INFORMATION: Back primer for amplification of murine
      variable regions, VH chain, of anti-Tirc7 antibody

<400> SEQUENCE: 15
gaataggcca tggcgcaggt tactctgaaa gagtc                               35

<210> SEQ ID NO 16
<211> LENGTH: 36
<212> TYPE: DNA
<213> ORGANISM: Artificial Sequence
<220> FEATURE:
<223> OTHER INFORMATION: Back primer for amplification of murine
      variable regions, VH chain, of anti-Tirc7 antibody

<400> SEQUENCE: 16
gaataggcca tggcggaggt ccagctgcaa caatct                              36

<210> SEQ ID NO 17
<211> LENGTH: 35
<212> TYPE: DNA
<213> ORGANISM: Artificial Sequence
<220> FEATURE:
<223> OTHER INFORMATION: Back primer for amplification of murine
      variable regions, VH chain, of anti-Tirc7 antibody

<400> SEQUENCE: 17
gaataggcca tggcggaggt ccagctgcag cagtc                               35

<210> SEQ ID NO 18
<211> LENGTH: 36
<212> TYPE: DNA
<213> ORGANISM: Artificial Sequence
<220> FEATURE:
<223> OTHER INFORMATION: Back primer for amplification of murine
      variable regions, VH chain, of anti-Tirc7 antibody

<400> SEQUENCE: 18
gaataggcca tggcgcaggt ccaactgcag cagcct                              36

<210> SEQ ID NO 19
<211> LENGTH: 35
<212> TYPE: DNA
<213> ORGANISM: Artificial Sequence
<220> FEATURE:
<223> OTHER INFORMATION: Back primer for amplification of murine
      variable regions, VH chain, of anti-Tirc7 antibody

<400> SEQUENCE: 19
gaataggcca tggcggaggt gaacctggtg gagtc                               35

<210> SEQ ID NO 20
<211> LENGTH: 35
<212> TYPE: DNA
<213> ORGANISM: Artificial Sequence
<220> FEATURE:
<223> OTHER INFORMATION: Back primer for amplification of murine
      variable regions, VH chain, of anti-Tirc7 antibody

<400> SEQUENCE: 20
gaataggcca tggcggaggt gaagctggtg gaatc                               35

```
<210> SEQ ID NO 21
<211> LENGTH: 35
<212> TYPE: DNA
<213> ORGANISM: Artificial Sequence
<220> FEATURE:
<223> OTHER INFORMATION: Back primer for amplification of murine
      variable regions, VH chain, of anti-Tirc7 antibody

<400> SEQUENCE: 21
gaataggcca tggcggatgt gaacttggaa gtgtc                          35

<210> SEQ ID NO 22
<211> LENGTH: 35
<212> TYPE: DNA
<213> ORGANISM: Artificial Sequence
<220> FEATURE:
<223> OTHER INFORMATION: Back primer for amplification of murine
      variable regions, VH chain, of anti-Tirc7 antibody

<400> SEQUENCE: 22
gaataggcca tggcggaggt ccagctgcaa cagtc                          35

<210> SEQ ID NO 23
<211> LENGTH: 35
<212> TYPE: DNA
<213> ORGANISM: Artificial Sequence
<220> FEATURE:
<223> OTHER INFORMATION: Back primer for amplification of murine
      variable regions, VH chain, of anti-Tirc7 antibody

<400> SEQUENCE: 23
gaataggcca tggcggaggt gcagctggag gagtc                          35

<210> SEQ ID NO 24
<211> LENGTH: 36
<212> TYPE: DNA
<213> ORGANISM: Artificial Sequence
<220> FEATURE:
<223> OTHER INFORMATION: Forward primer of murine variable regions, VH
      chain, of anti-Tirc7 antibody

<400> SEQUENCE: 24
ggccagtgga taaacctttg ggggtgtcgt tttggc                         36

<210> SEQ ID NO 25
<211> LENGTH: 38
<212> TYPE: DNA
<213> ORGANISM: Artificial Sequence
<220> FEATURE:
<223> OTHER INFORMATION: Back primer of murine variable regions,
      VH chain, of anti-Tirc7 antibody

<400> SEQUENCE: 25
tacaggatcc acgcgtagat gttttgatga cccaaact                       38

<210> SEQ ID NO 26
<211> LENGTH: 38
<212> TYPE: DNA
<213> ORGANISM: Artificial Sequence
<220> FEATURE:
<223> OTHER INFORMATION: Back primer of murine variable regions,
      VH chain, of anti-Tirc7 antibody

<400> SEQUENCE: 26
tacaggatcc acgcgtagat attgtgatga cgcaggct                       38
```

<210> SEQ ID NO 27
<211> LENGTH: 35
<212> TYPE: DNA
<213> ORGANISM: Artificial Sequence
<220> FEATURE:
<223> OTHER INFORMATION: Back primer of murine variable regions,
      VH chain, of anti-Tirc7 antibody

<400> SEQUENCE: 27
tacaggatcc acgcgtagat attgtgataa cccag                        35

<210> SEQ ID NO 28
<211> LENGTH: 38
<212> TYPE: DNA
<213> ORGANISM: Artificial Sequence
<220> FEATURE:
<223> OTHER INFORMATION: Back primer of murine variable regions,
      VH chain, of anti-Tirc7 antibody

<400> SEQUENCE: 28
tacaggatcc acgcgtagac attgtgctga cccaatct                     38

<210> SEQ ID NO 29
<211> LENGTH: 38
<212> TYPE: DNA
<213> ORGANISM: Artificial Sequence
<220> FEATURE:
<223> OTHER INFORMATION: Back primer of murine variable regions,
      VH chain, of anti-Tirc7 antibody

<400> SEQUENCE: 29
tacaggatcc acgcgtagac attgtgatga cccagtct                     38

<210> SEQ ID NO 30
<211> LENGTH: 38
<212> TYPE: DNA
<213> ORGANISM: Artificial Sequence
<220> FEATURE:
<223> OTHER INFORMATION: Back primer of murine variable regions,
      VH chain, of anti-Tirc7 antibody

<400> SEQUENCE: 30
tacaggatcc acgcgtagat attgtgctaa ctcagtct                     38

<210> SEQ ID NO 31
<211> LENGTH: 38
<212> TYPE: DNA
<213> ORGANISM: Artificial Sequence
<220> FEATURE:
<223> OTHER INFORMATION: Back primer of murine variable regions,
      VH chain, of anti-Tirc7 antibody

<400> SEQUENCE: 31
tacaggatcc acgcgtagat atccagatga cacagact                     38

<210> SEQ ID NO 32
<211> LENGTH: 38
<212> TYPE: DNA
<213> ORGANISM: Artificial Sequence
<220> FEATURE:
<223> OTHER INFORMATION: Back primer of murine variable regions,
      VH chain, of anti-Tirc7 antibody

<400> SEQUENCE: 32
tacaggatcc acgcgtagac atccagctga ctcagtct                     38

<210> SEQ ID NO 33

```
<211> LENGTH: 38
<212> TYPE: DNA
<213> ORGANISM: Artificial Sequence
<220> FEATURE:
<223> OTHER INFORMATION: Back primer of murine variable regions,
      VH chain, of anti-Tirc7 antibody

<400> SEQUENCE: 33
tacaggatcc acgcgtacaa attgttctca cccagtct                              38

<210> SEQ ID NO 34
<211> LENGTH: 38
<212> TYPE: DNA
<213> ORGANISM: Artificial Sequence
<220> FEATURE:
<223> OTHER INFORMATION: Back primer of murine variable regions,
      VH chain, of anti-Tirc7 antibody

<400> SEQUENCE: 34
tacaggatcc acgcgtagac attctgatga cccagtct                              38

<210> SEQ ID NO 35
<211> LENGTH: 39
<212> TYPE: DNA
<213> ORGANISM: Artificial Sequence
<220> FEATURE:
<223> OTHER INFORMATION: Forward primer of murine variable regions, VL
      chain, of anti-Tirc7 antibody

<400> SEQUENCE: 35
tgacaagctt gcggccgcgg atacagttgg tgcagcatc                             39

<210> SEQ ID NO 36
<211> LENGTH: 98
<212> TYPE: DNA
<213> ORGANISM: Artificial Sequence
<220> FEATURE:
<223> OTHER INFORMATION: 5' primer for cloning VH chain of murine
      anti-Tirc7 anitbody in pConGamma1f vector

<400> SEQUENCE: 36
gcgcgcaagc ttgccgccac catgggatgg agctgtatca tcctcttctt ggtagcaaca     60
gctacaggtg tccactccga ggtgcagctg caacagtc                             98

<210> SEQ ID NO 37
<211> LENGTH: 45
<212> TYPE: DNA
<213> ORGANISM: Artificial Sequence
<220> FEATURE:
<223> OTHER INFORMATION: 3' primer for cloning VH chain of murine
      anti-Tirc7 anitbody in pConGamma1f vector

<400> SEQUENCE: 37
tttatatggg cccttggtgg aggctgagga gacggtgacc gtggt                     45

<210> SEQ ID NO 38
<211> LENGTH: 99
<212> TYPE: DNA
<213> ORGANISM: Artificial Sequence
<220> FEATURE:
<223> OTHER INFORMATION: 5' primer for cloning VH chain of murine
      anti-Tirc7 anitbody in pConKappa vector

<400> SEQUENCE: 38
gcgcgcaagc ttgccgccac catgggatgg agctgtatca tcctcttctt ggtagcaaca     60
gctacaggtg tccactccca aattgttctc acccagtct                            99
```

```
<210> SEQ ID NO 39
<211> LENGTH: 33
<212> TYPE: DNA
<213> ORGANISM: Artificial Sequence
<220> FEATURE:
<223> OTHER INFORMATION: 3' primer for cloning VH chain of anti-Tirc7
      anitbody in pConGamma1f vector

<400> SEQUENCE: 39
atatggcgta cgtttgattt ccaacttggt gcc                              33

<210> SEQ ID NO 40
<211> LENGTH: 35
<212> TYPE: DNA
<213> ORGANISM: Artificial Sequence
<220> FEATURE:
<223> OTHER INFORMATION: Back primer for amplification of murine
      variable regions, VH chain, of anti-Tirc7 antibody

<400> SEQUENCE: 40
gaataggcca tggcggatgt gaagctgcag gagtc                            35

<210> SEQ ID NO 41
<211> LENGTH: 26
<212> TYPE: DNA
<213> ORGANISM: Artificial Sequence
<220> FEATURE:
<223> OTHER INFORMATION: Primer for cDNA synthesis of VH region of
      murine anti-Tirc7 antibody

<400> SEQUENCE: 41
cacaattttc ttgtccacct tggtgc                                      26

<210> SEQ ID NO 42
<211> LENGTH: 27
<212> TYPE: DNA
<213> ORGANISM: Artificial Sequence
<220> FEATURE:
<223> OTHER INFORMATION: Primer for cDNA synthesis of VL region of
      murine anti-Tirc7 antibody

<400> SEQUENCE: 42
ctcaatcctg ttgaagctct tgacaat                                     27
```